United States Patent
Kasai et al.

(10) Patent No.: US 7,907,744 B2
(45) Date of Patent: Mar. 15, 2011

(54) CAPACITIVE VIBRATION SENSOR AND METHOD FOR MANUFACTURING SAME

(75) Inventors: Takashi Kasai, Nara (JP); Fumihito Kato, Hatogaya (JP); Hiroshi Imamoto, Konan (JP); Fumihiko Sato, Tsuchiura (JP); Masaki Munechika, Nara (JP); Toshiyuki Takahashi, Nara (JP)

(73) Assignee: OMRON Corporation, Kyoto (JP)

( * ) Notice: Subject to any disclaimer, the term of this patent is extended or adjusted under 35 U.S.C. 154(b) by 906 days.

(21) Appl. No.: 11/666,951

(22) PCT Filed: Oct. 28, 2005

(86) PCT No.: PCT/JP2005/019893
§ 371 (c)(1),
(2), (4) Date: Jul. 20, 2007

(87) PCT Pub. No.: WO2006/049100
PCT Pub. Date: May 11, 2006

(65) Prior Publication Data
US 2007/0261910 A1    Nov. 15, 2007

(30) Foreign Application Priority Data

Nov. 4, 2004  (JP) ................... 2004-320732
Jun. 13, 2005  (JP) ................... 2005-171763

(51) Int. Cl.
*H04R 25/00* (2006.01)
(52) U.S. Cl. ....................... 381/174; 381/175
(58) Field of Classification Search .......... 381/173–175, 381/190–191, 369; 367/174, 181, 188
See application file for complete search history.

(56) References Cited

U.S. PATENT DOCUMENTS

| 4,456,796 A | * | 6/1984 | Nakagawa et al. | ........... 381/191 |
| 4,776,019 A | | 10/1988 | Miyatake et al. | |
| 5,146,435 A | | 9/1992 | Bernstein | |
| 5,303,210 A | * | 4/1994 | Bernstein | ........... 367/181 |
| 6,088,463 A | * | 7/2000 | Rombach et al. | ........... 381/174 |

(Continued)

FOREIGN PATENT DOCUMENTS

JP     62-284233     12/1987

(Continued)

OTHER PUBLICATIONS

International Search Report issued in PCT/JP2005/019893 mailed on Feb. 7, 2006 with translation, 4 pages.

*Primary Examiner* — Suhan Ni
(74) *Attorney, Agent, or Firm* — Osha • Liang LLP

(57) ABSTRACT

A vibration electrode plate 112 is formed on the upper face of a silicon substrate 32 with an insulating coat film 35 interposed in between. An opposing electrode plate 113 is placed on the vibration electrode plate 112 with an insulating coat film interposed in between, and acoustic holes 40 are opened through the opposing electrode plate 113. Etching holes 36 and 104, each having a semi-elliptical shape, are opened through the vibration electrode plate 112 and the opposing electrode plate 113 so as to face each other longitudinally. A concave section 37 having a truncated pyramid shape is formed in the upper face of the silicon substrate 32, by carrying out an etching process through the etching holes 36 and 104. The vibration electrode plate 112 is held in the silicon substrate 32 by a holding portion 112 placed between the etching holes 36.

16 Claims, 37 Drawing Sheets

| U.S. PATENT DOCUMENTS | | | | |
|---|---|---|---|---|
| 6,178,249 B1 * | 1/2001 | Hietanen et al. | | 381/174 |
| 7,031,480 B2 * | 4/2006 | Himori et al. | | 381/174 |
| 7,221,767 B2 * | 5/2007 | Mullenborn et al. | | 381/174 |

| FOREIGN PATENT DOCUMENTS | | |
|---|---|---|
| JP | 04-127479 | 4/1992 |
| JP | 09-082983 | 3/1997 |
| JP | 09-130199 | 5/1997 |
| JP | 09-508777 | 9/1997 |
| JP | 2001-013156 | 1/2001 |
| JP | 2001-518246 | 10/2001 |
| JP | 2002-027595 | 1/2002 |
| JP | 2003-508998 | 3/2003 |
| JP | 2004-506394 | 2/2004 |
| JP | 2004-128957 | 4/2004 |
| WO | WO-96/05711 | 2/1996 |
| WO | WO-98/37388 | 8/1998 |
| WO | WO-01/19134 A2 | 3/2001 |
| WO | WO-02/15636 A2 | 2/2002 |

* cited by examiner

[Fig. 1]
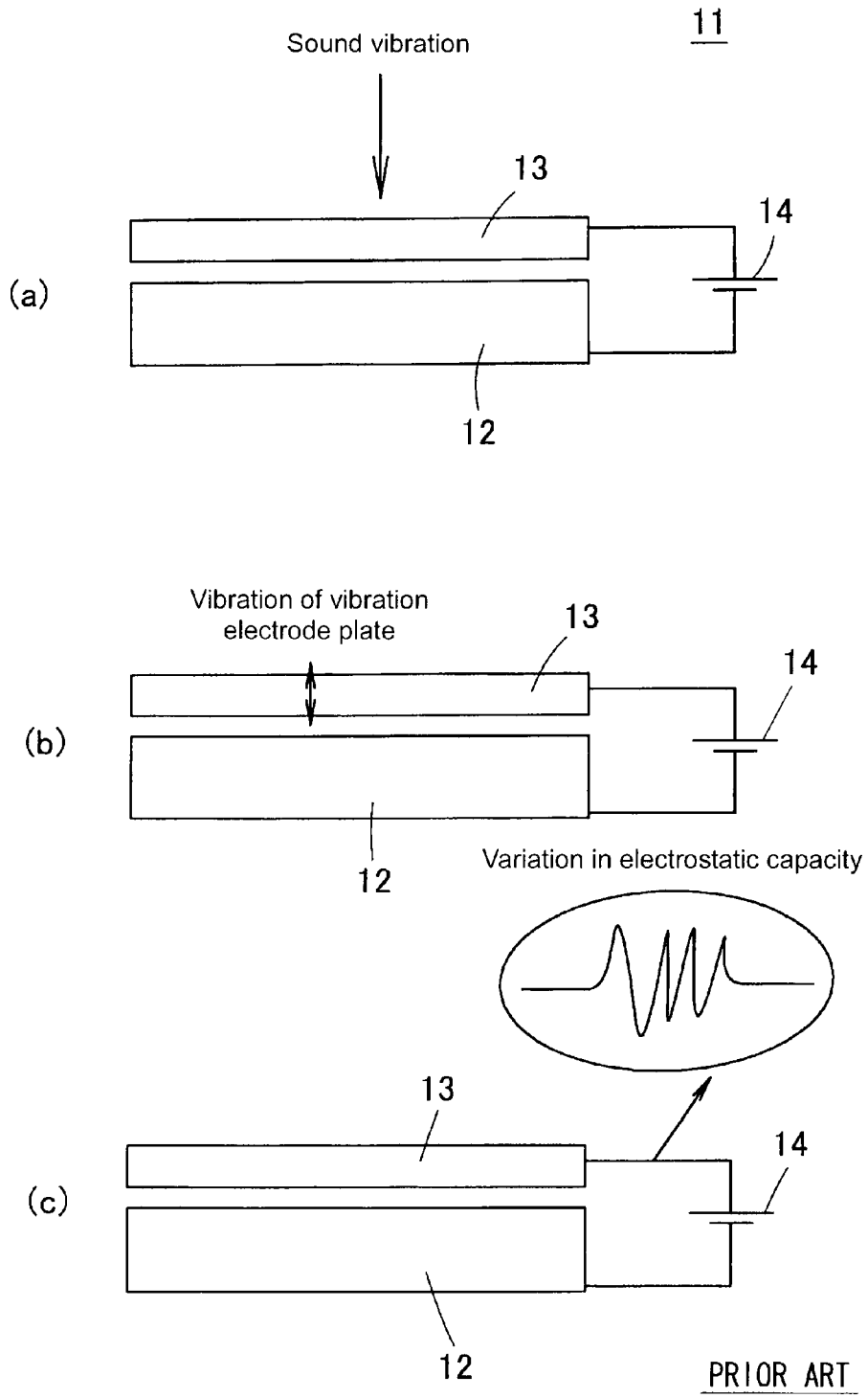

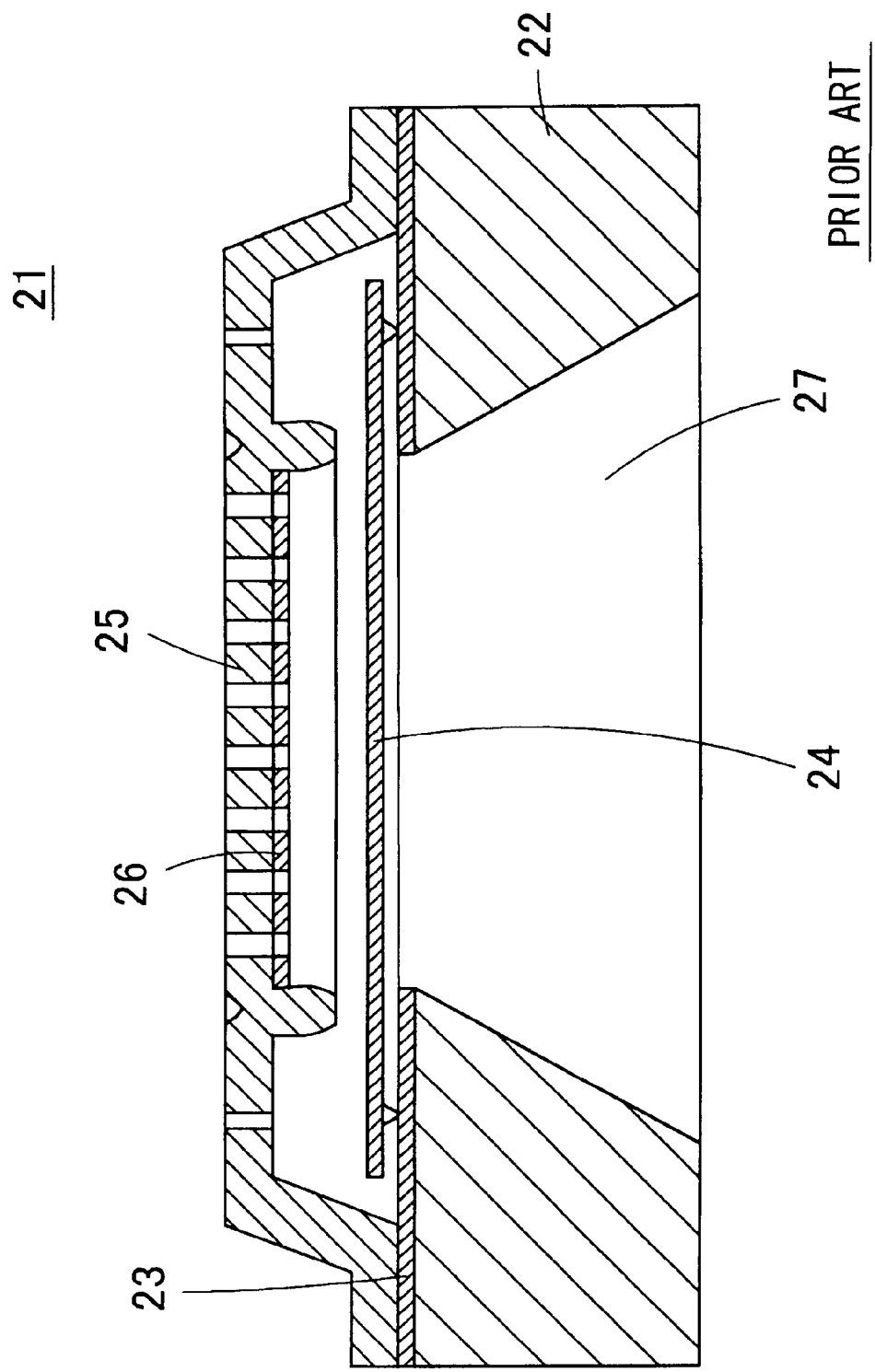
[Fig. 2]
PRIOR ART

[Fig. 3]
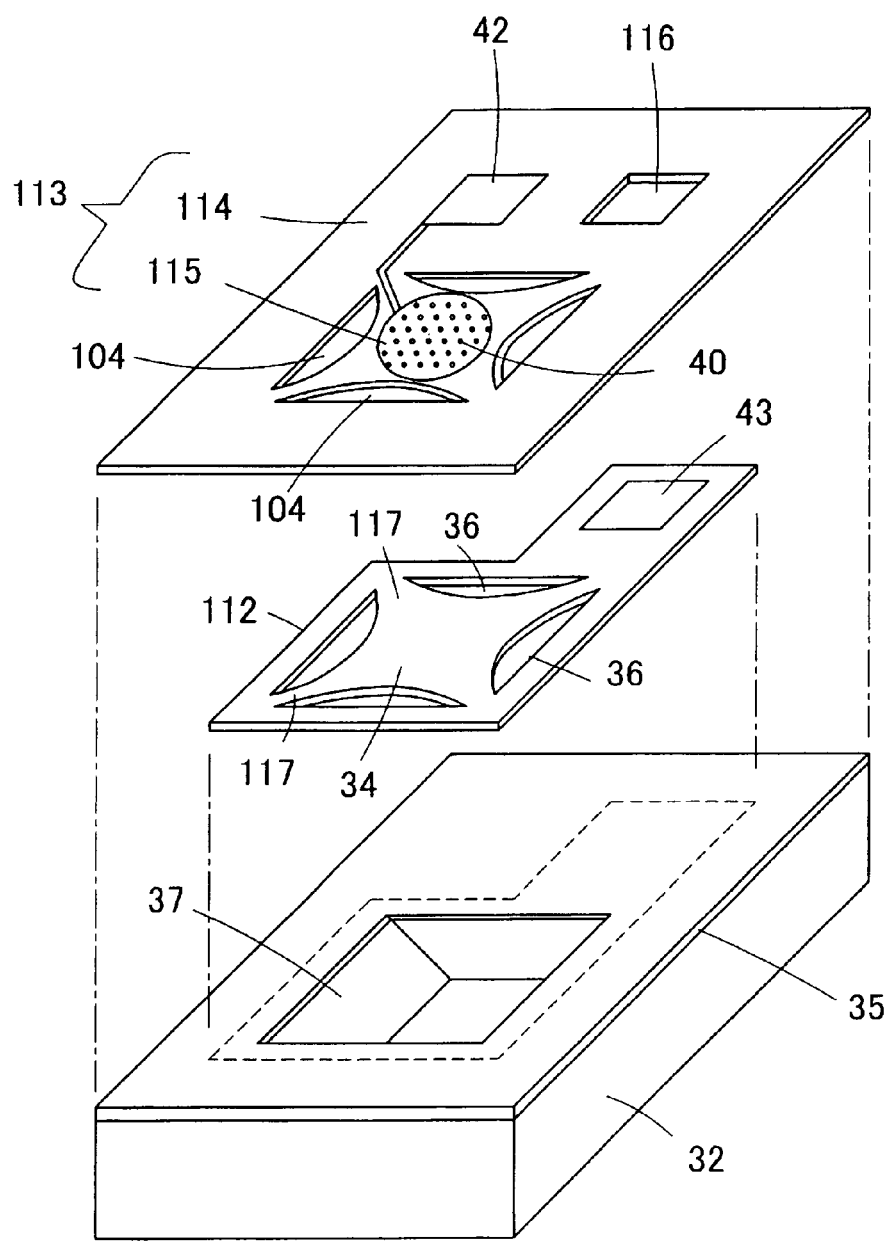

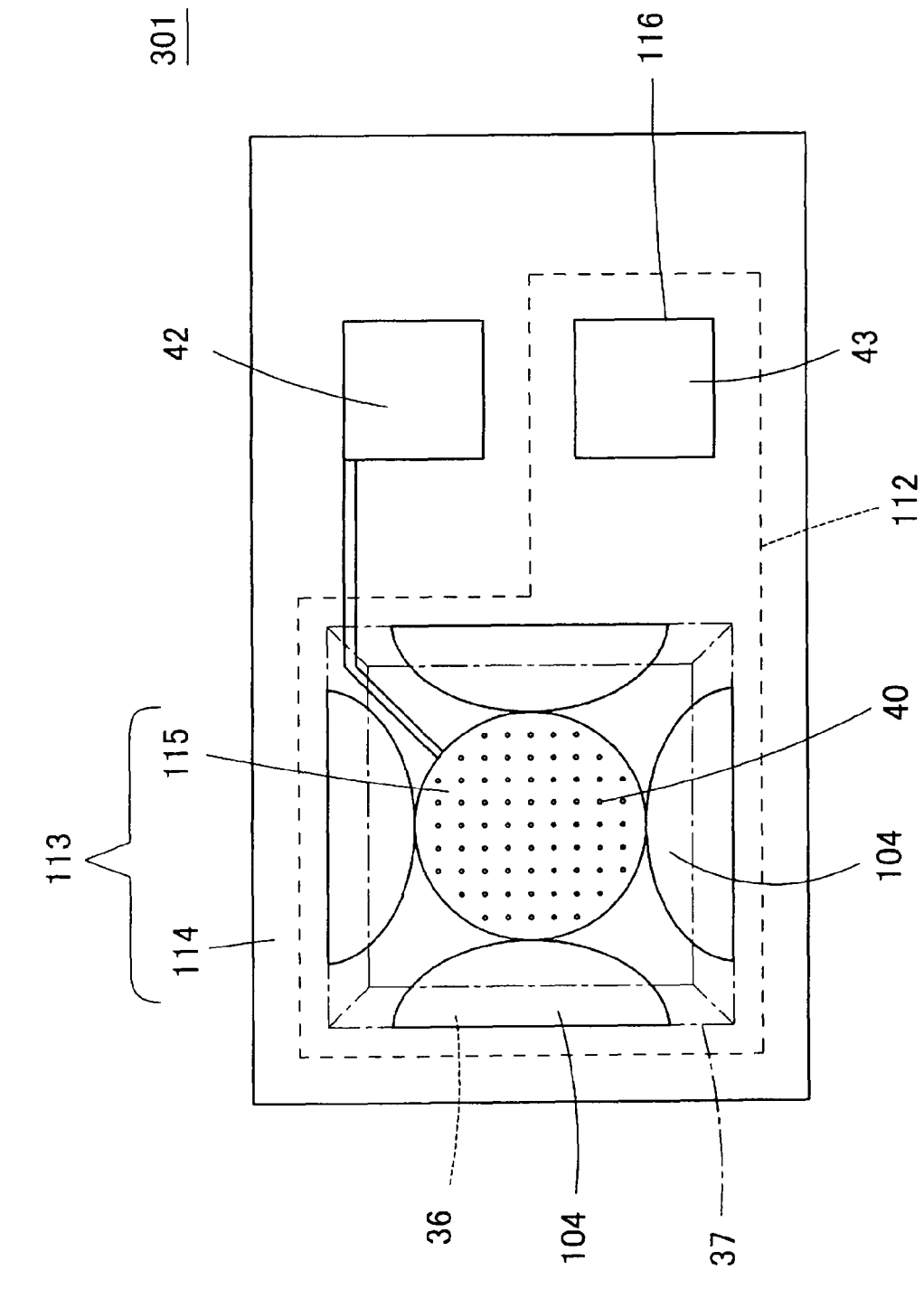

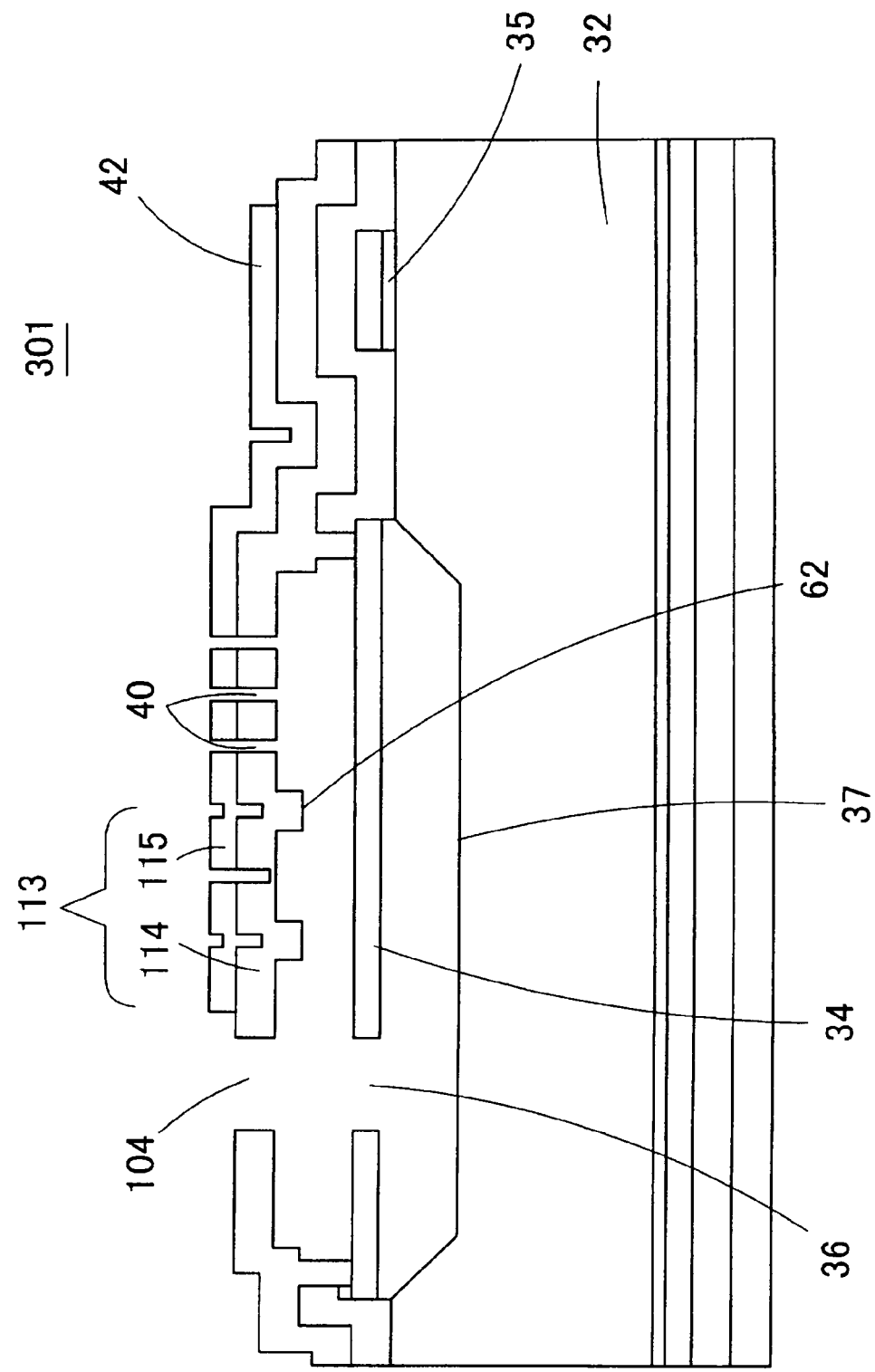

[Fig. 6]
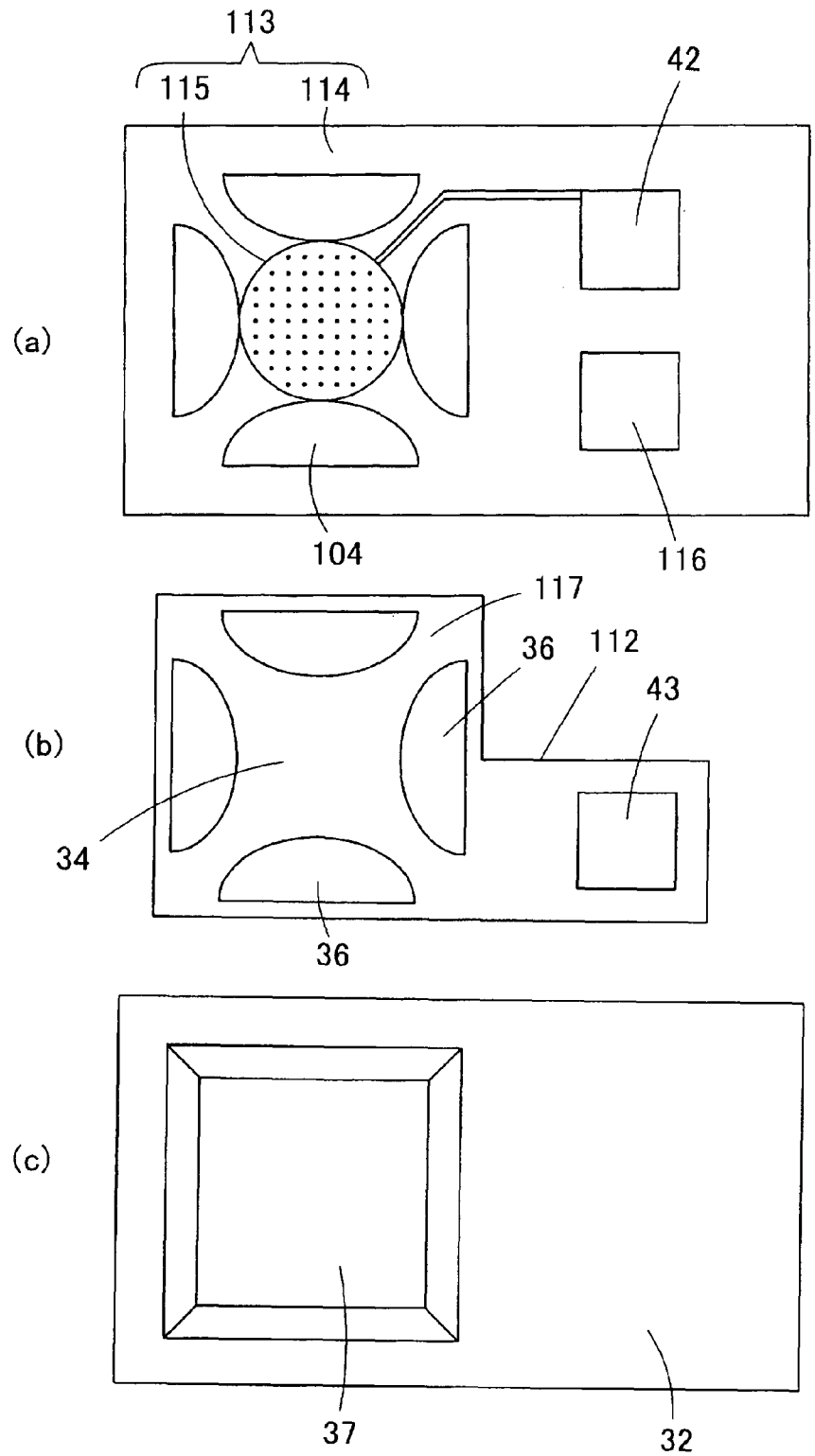

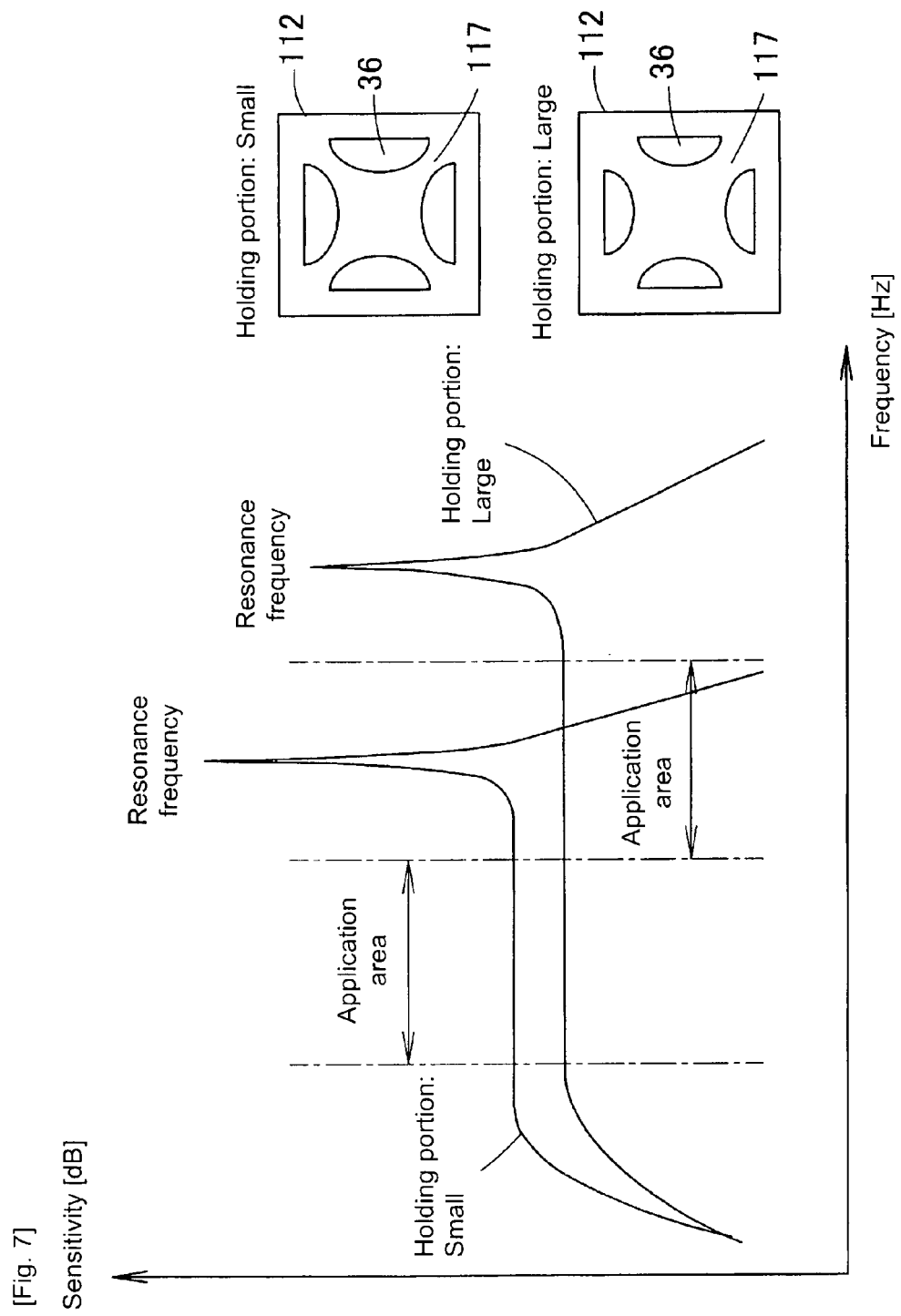
[Fig. 7]

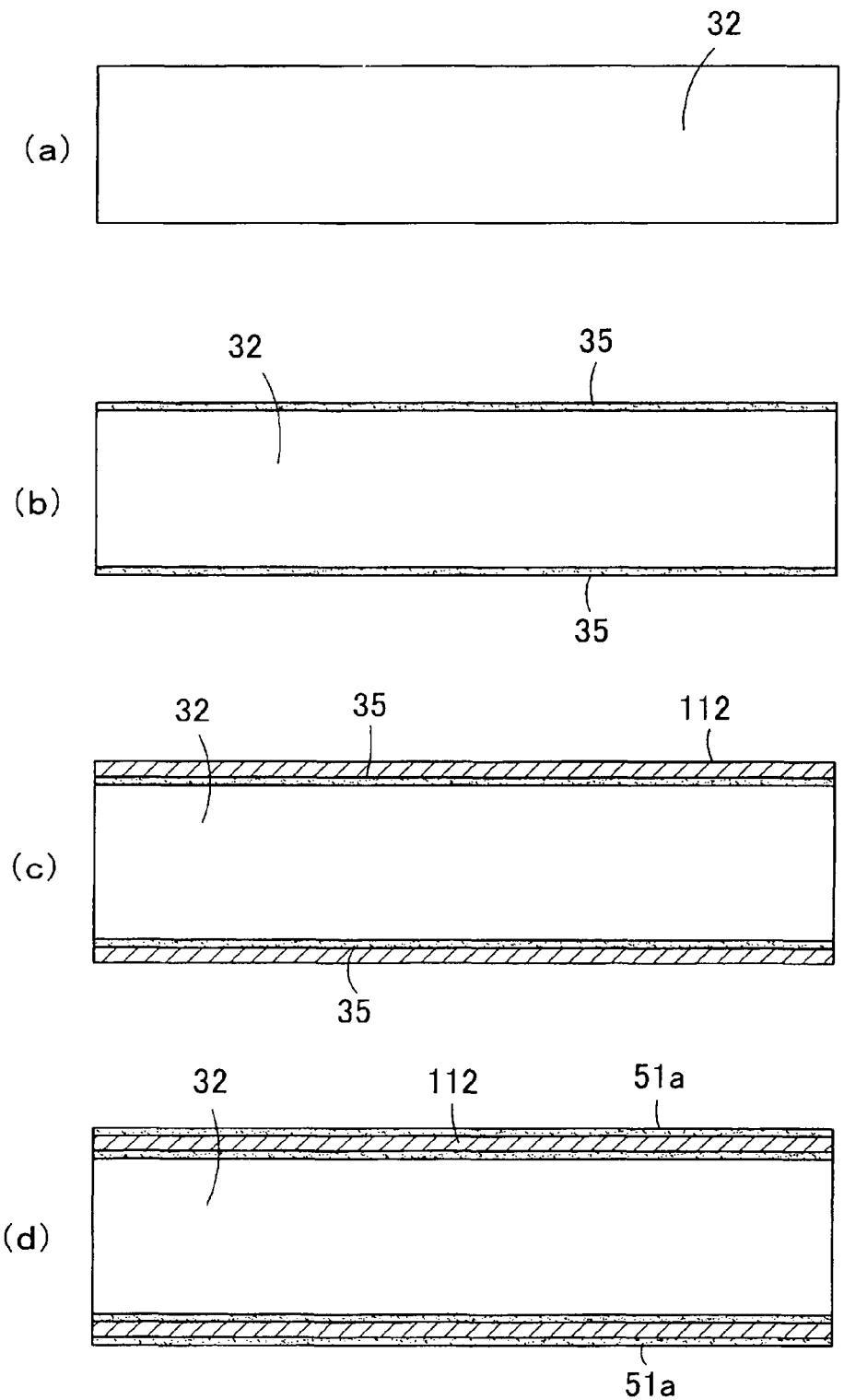
[Fig. 8]

[Fig. 9]
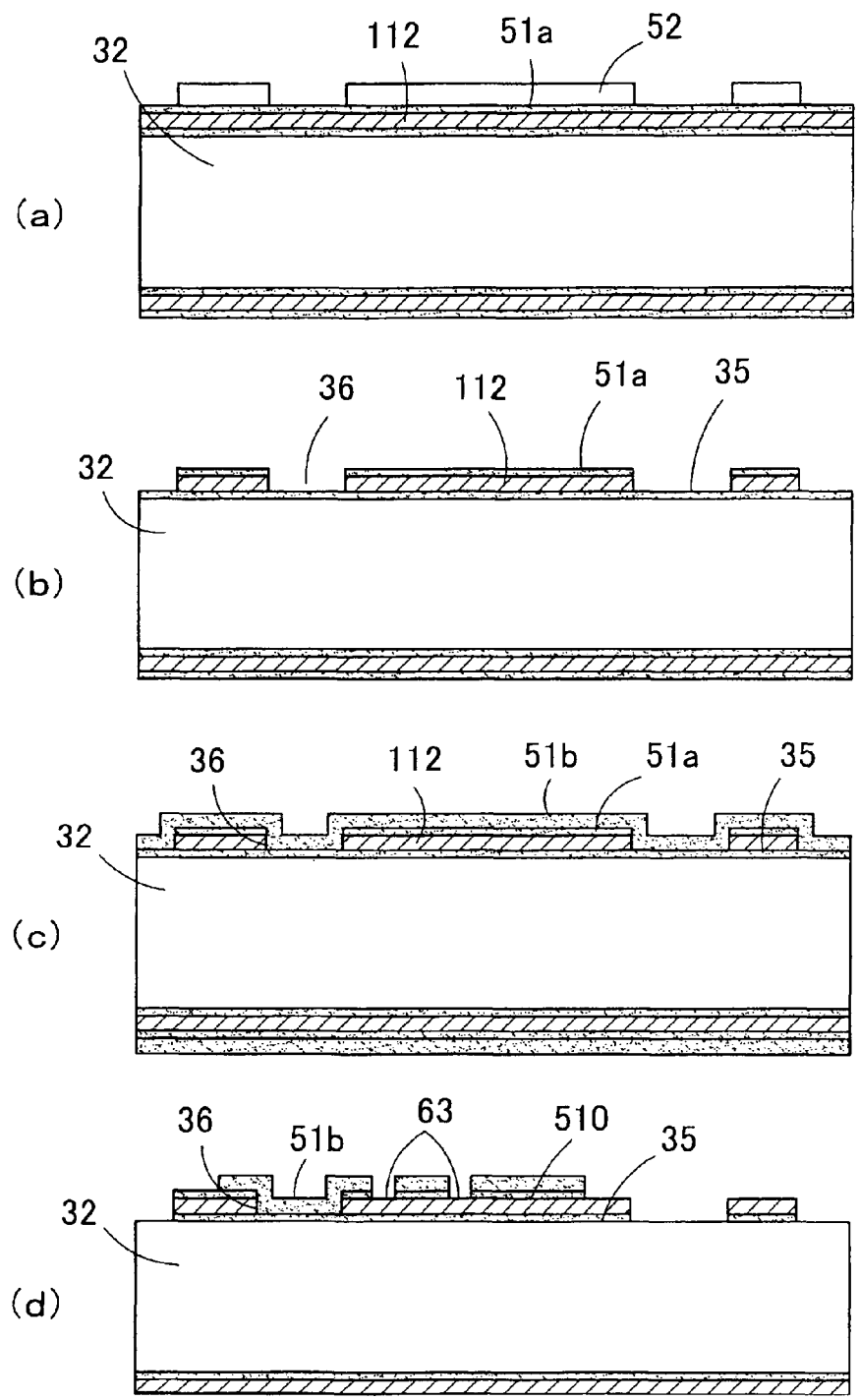

[Fig. 10]
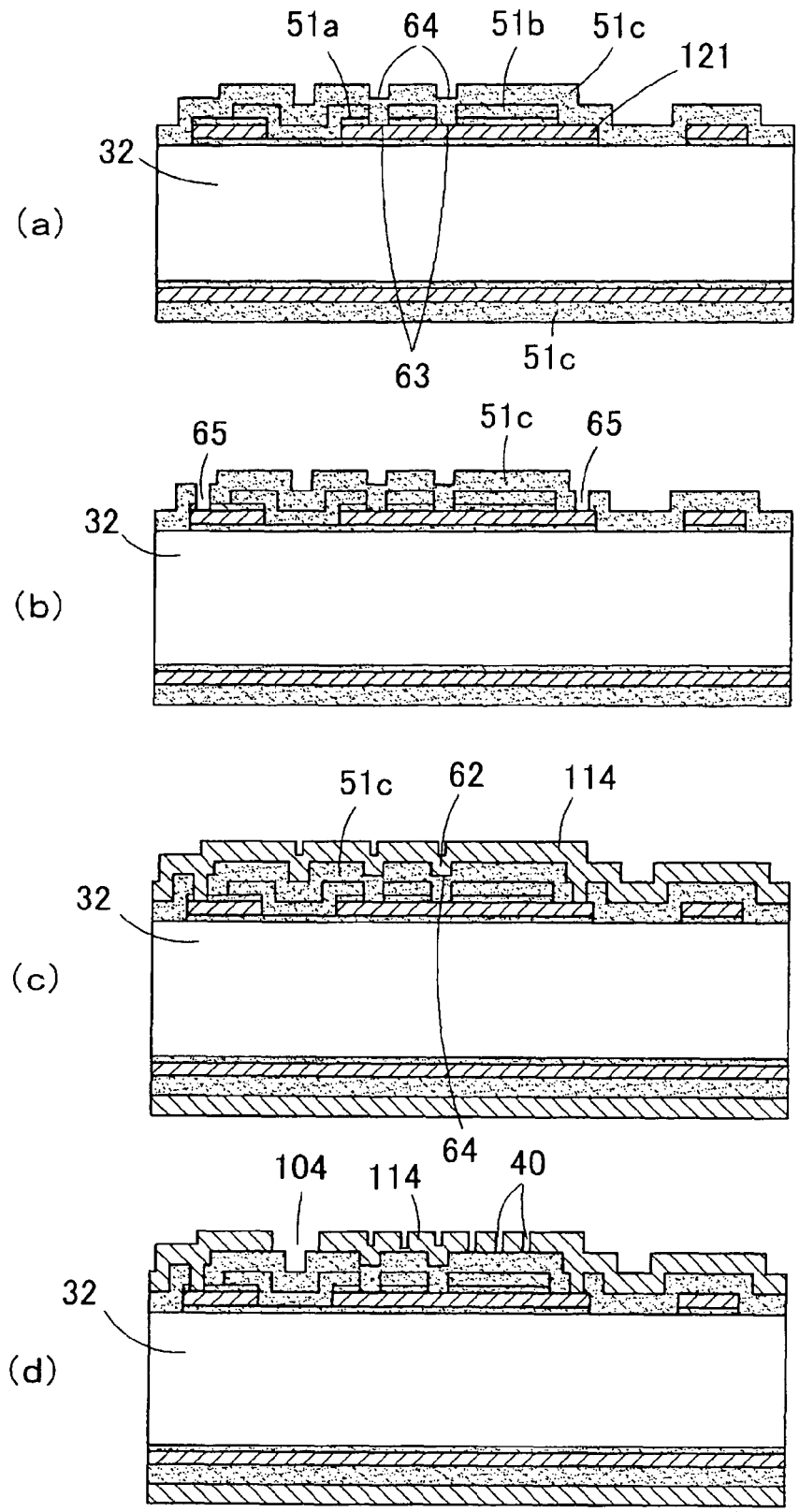

[Fig. 11]
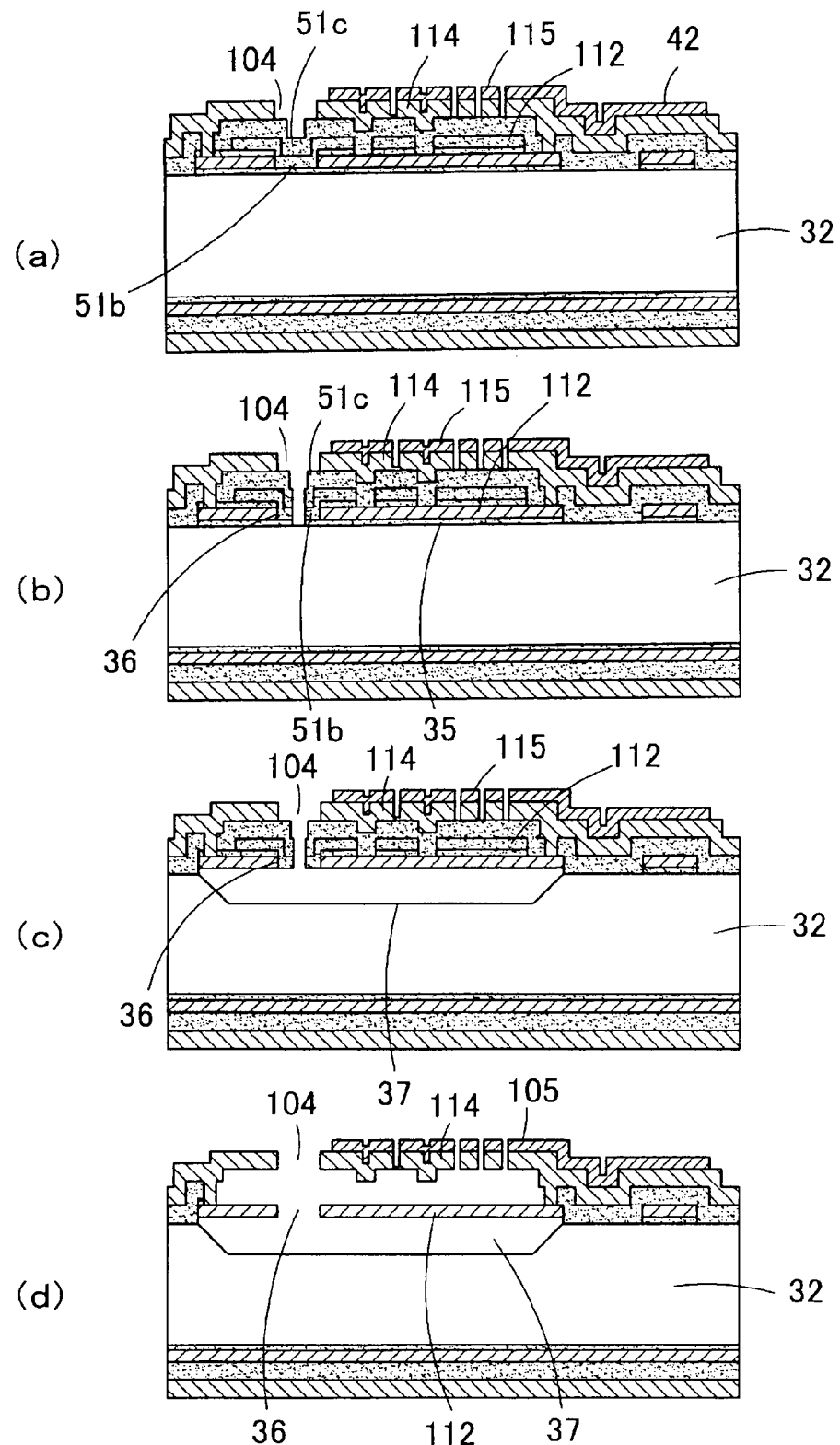

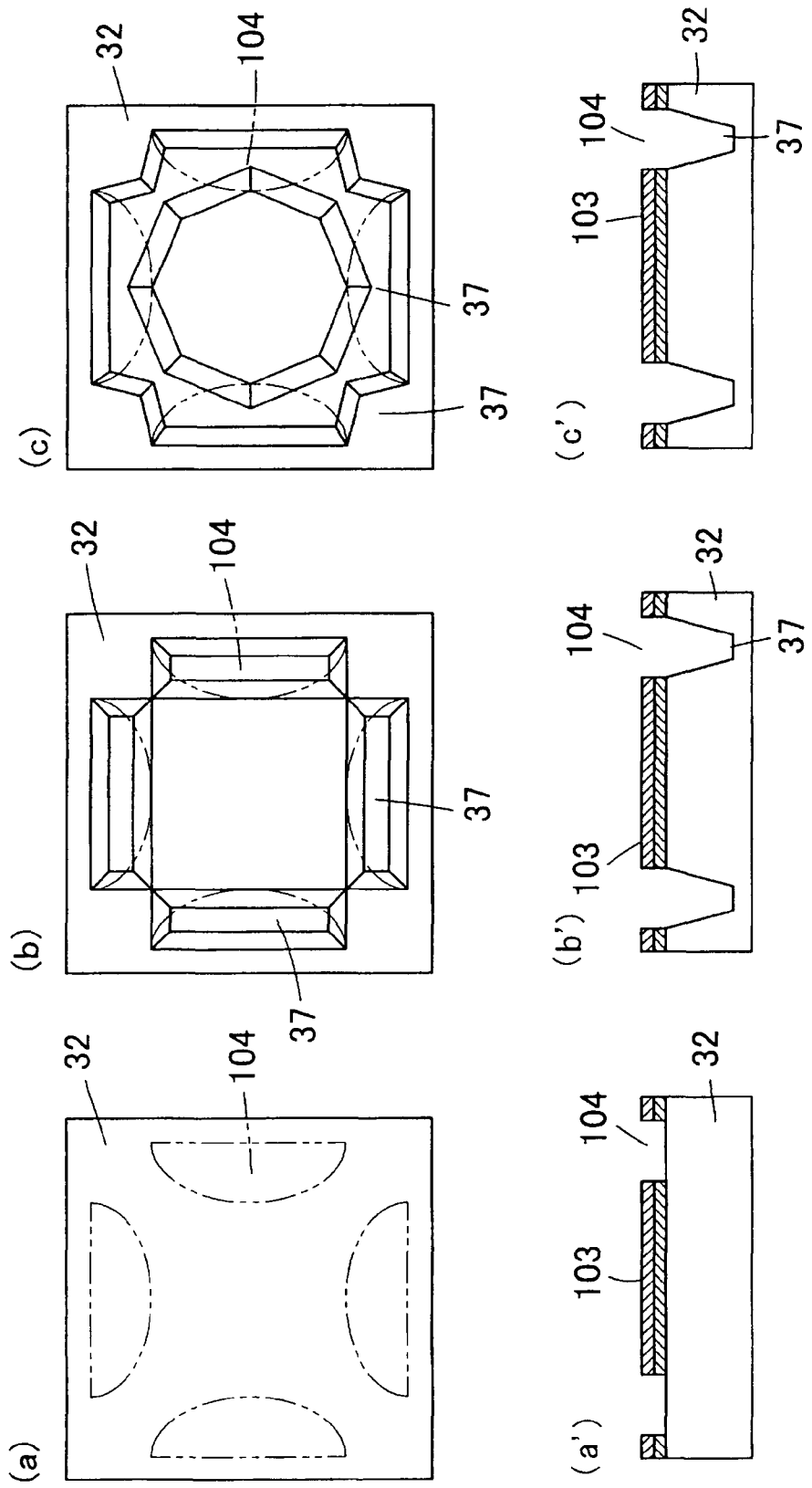
[Fig. 12]

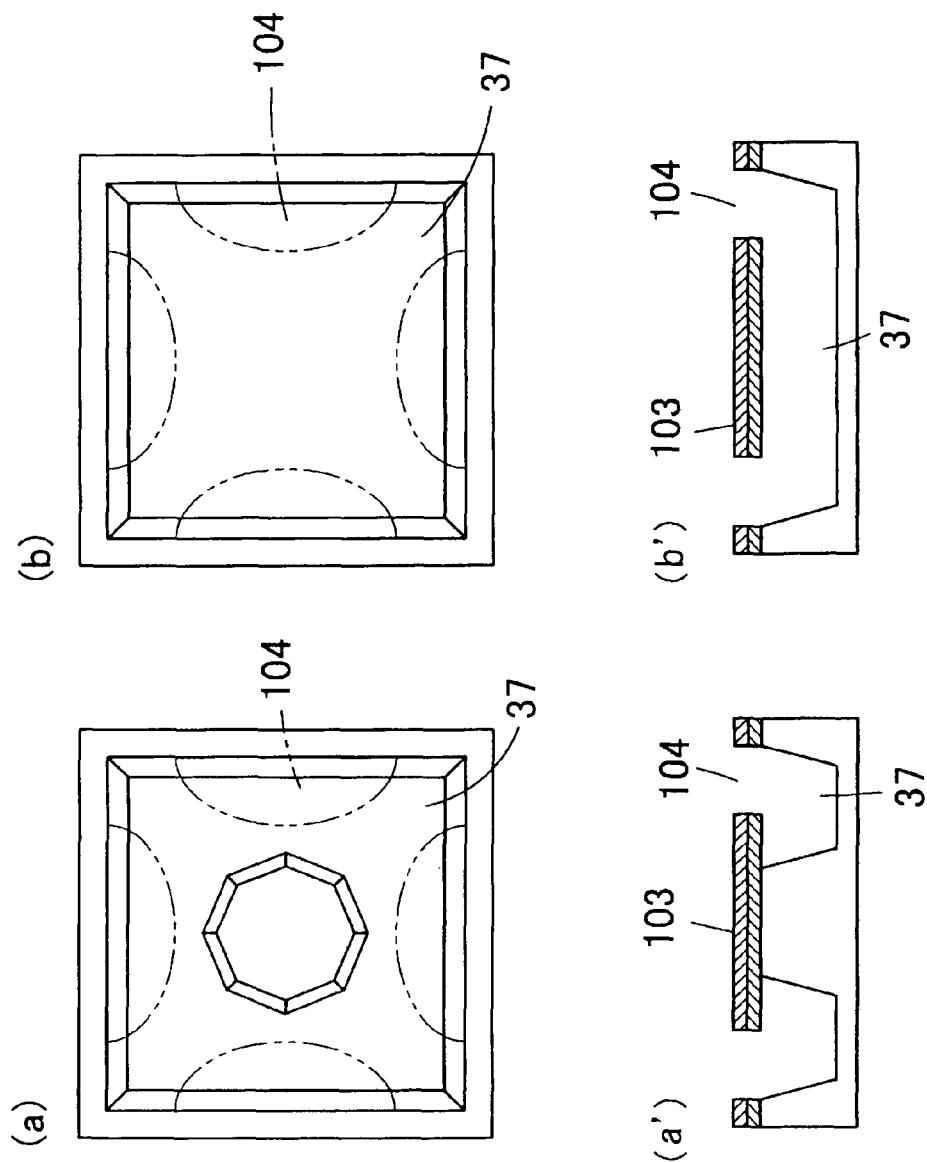
[Fig. 13]

[Fig. 14]
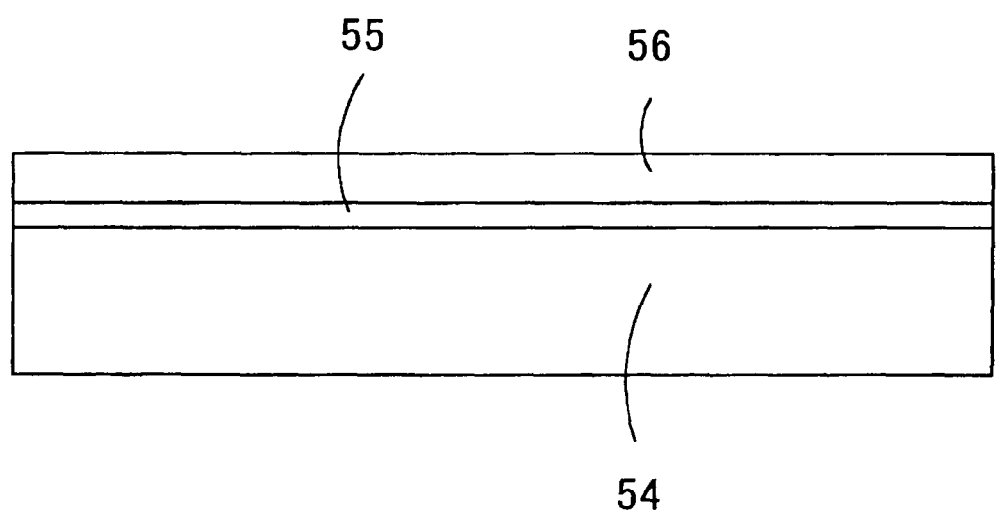

[Fig. 15]
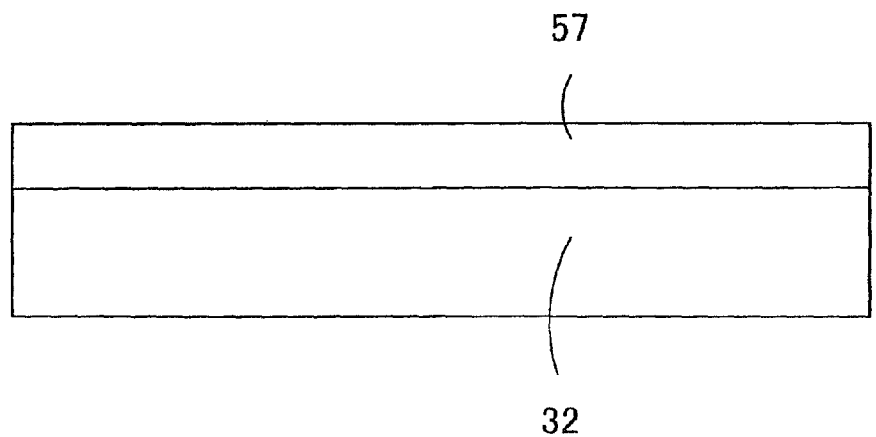

[Fig. 16]
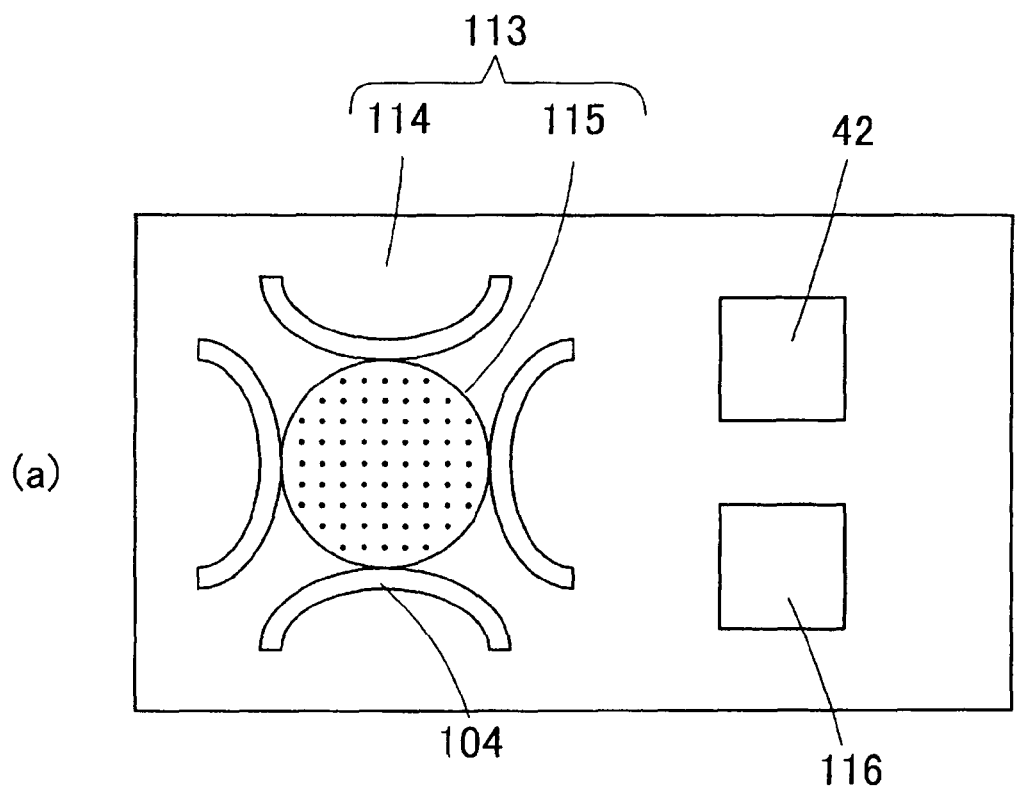
(a)
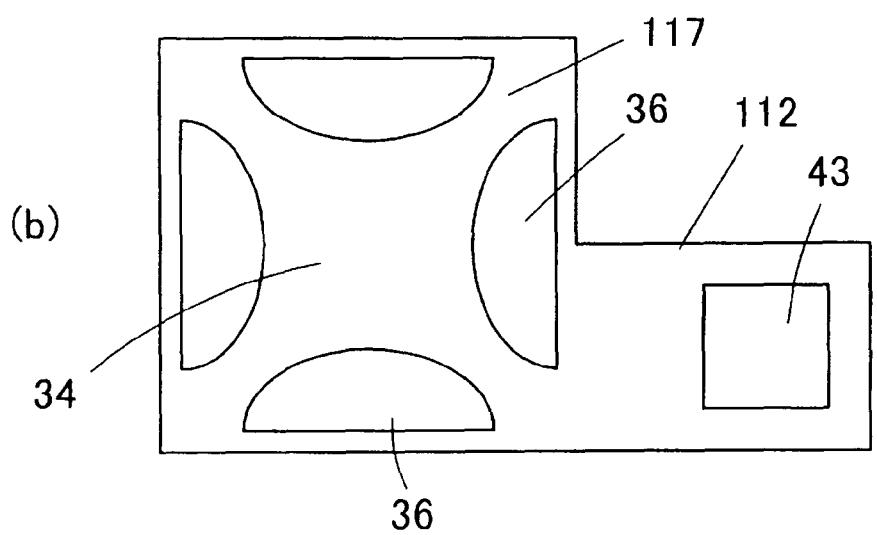
(b)

[Fig. 17]
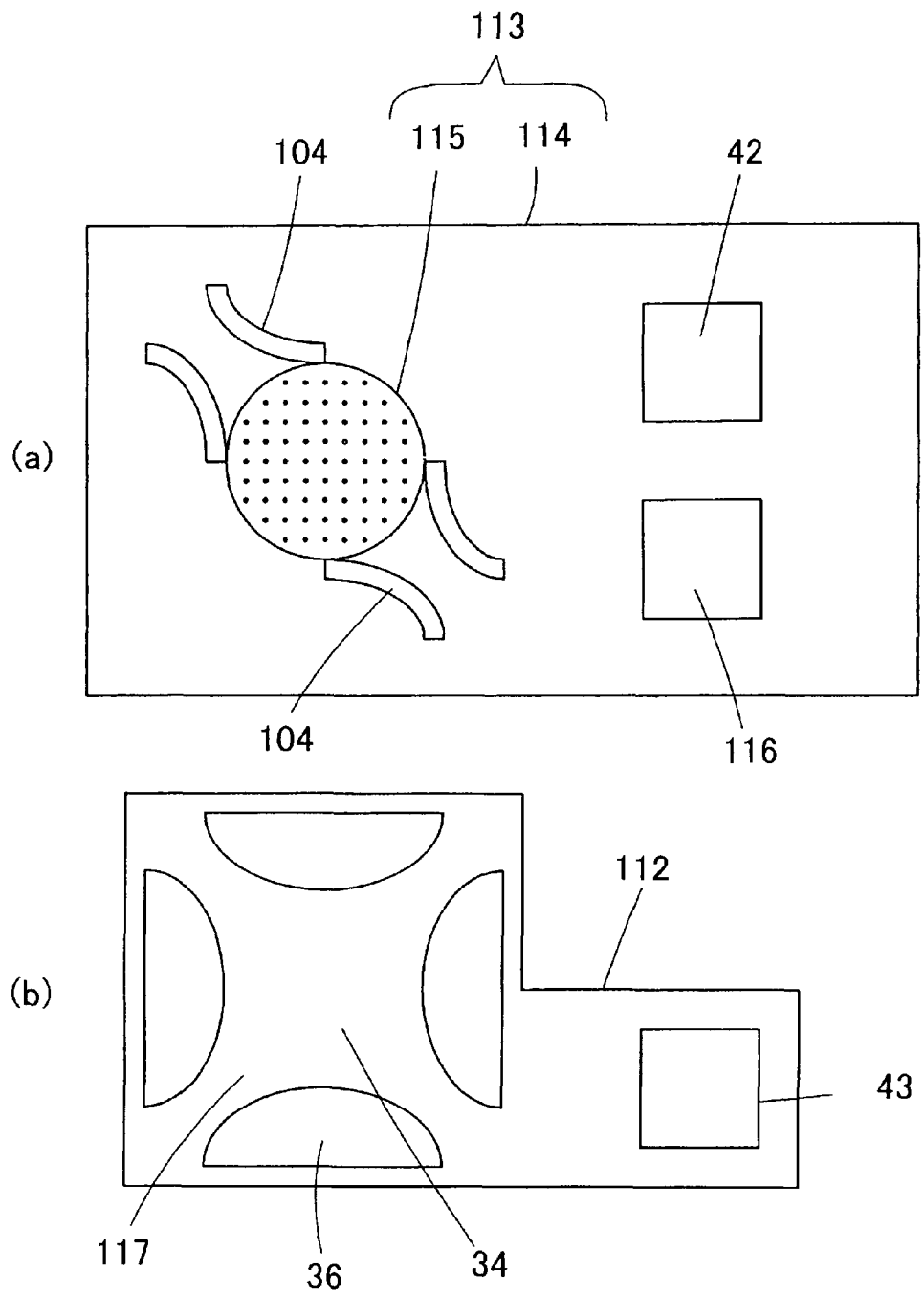

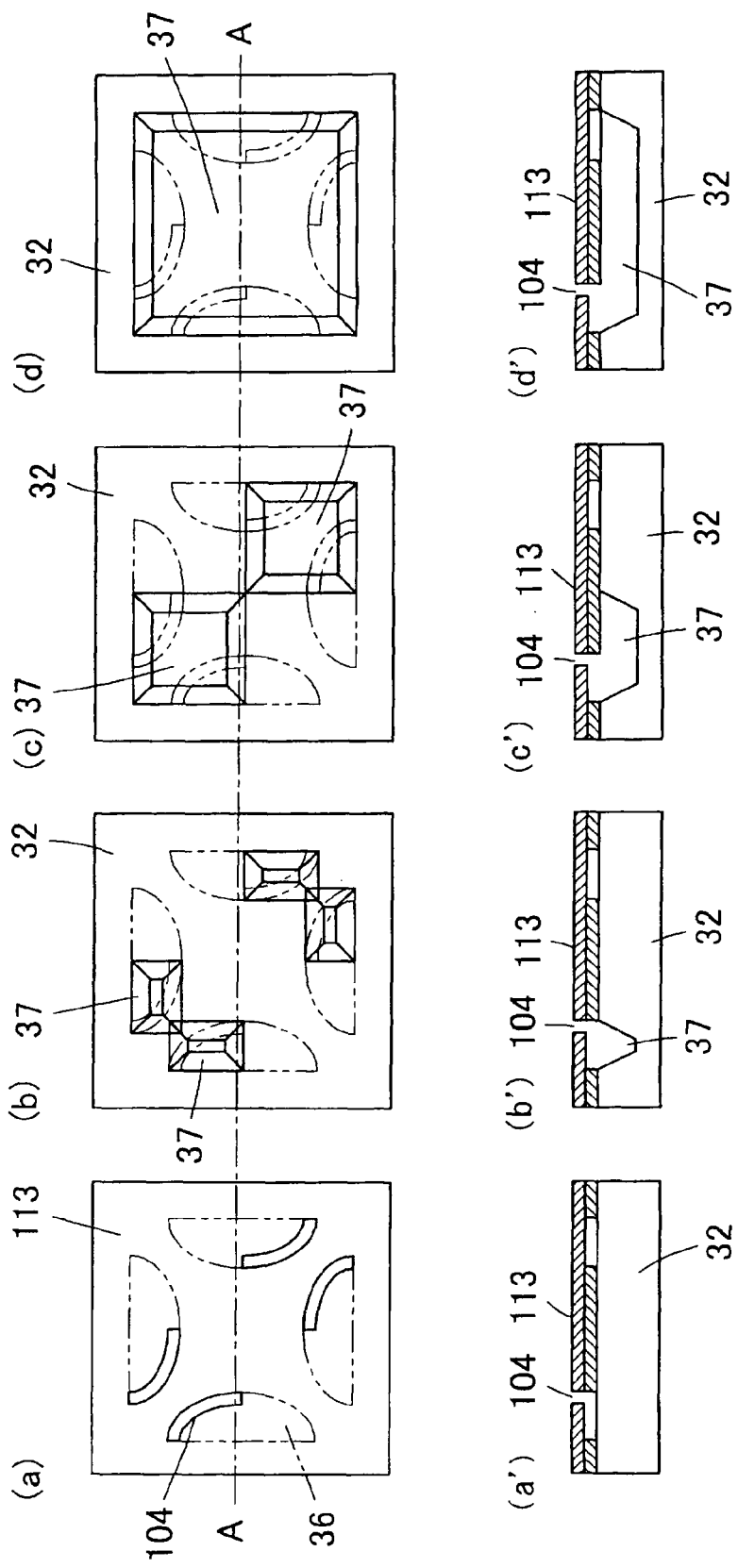

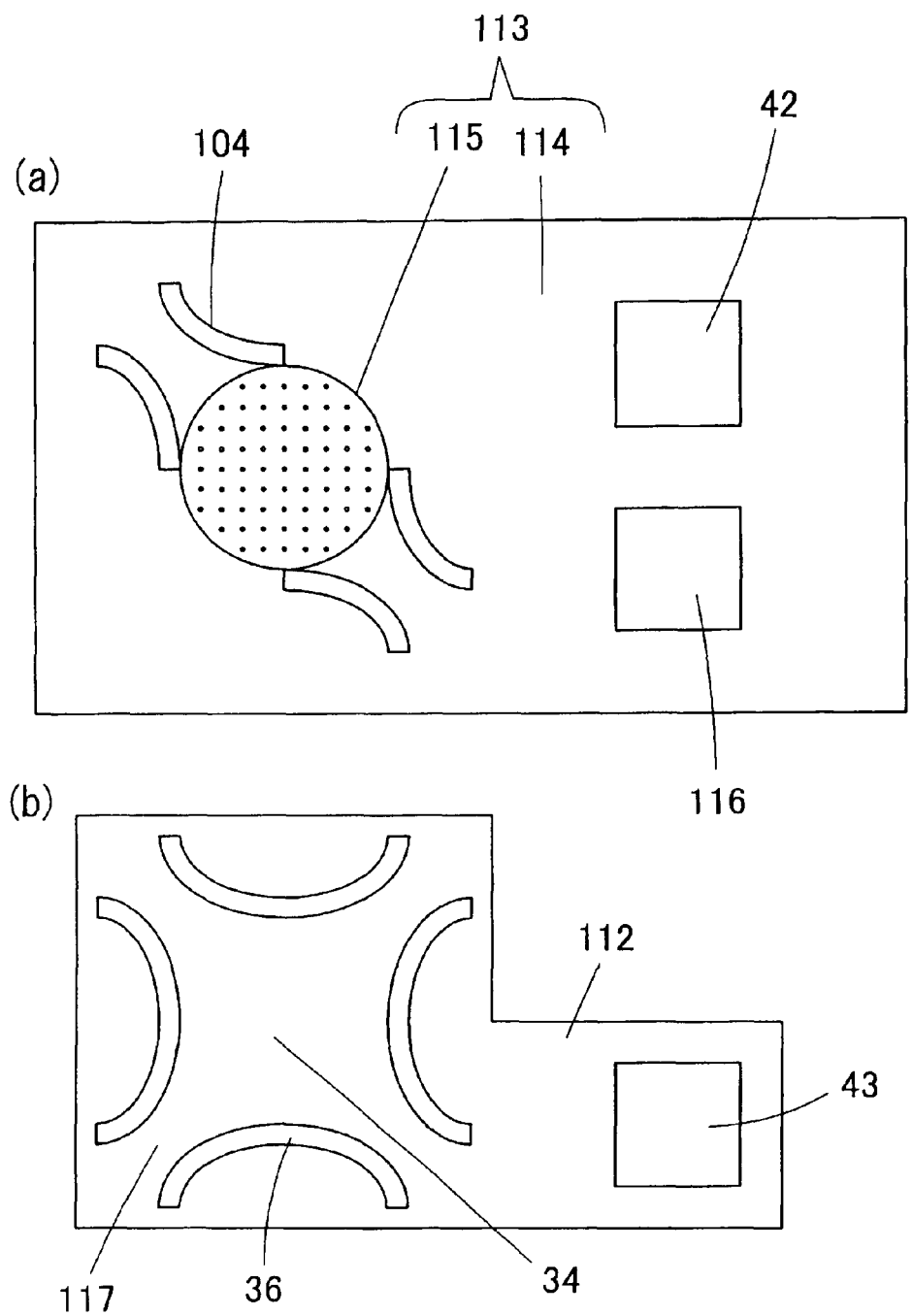
[Fig. 19]

[Fig. 20]
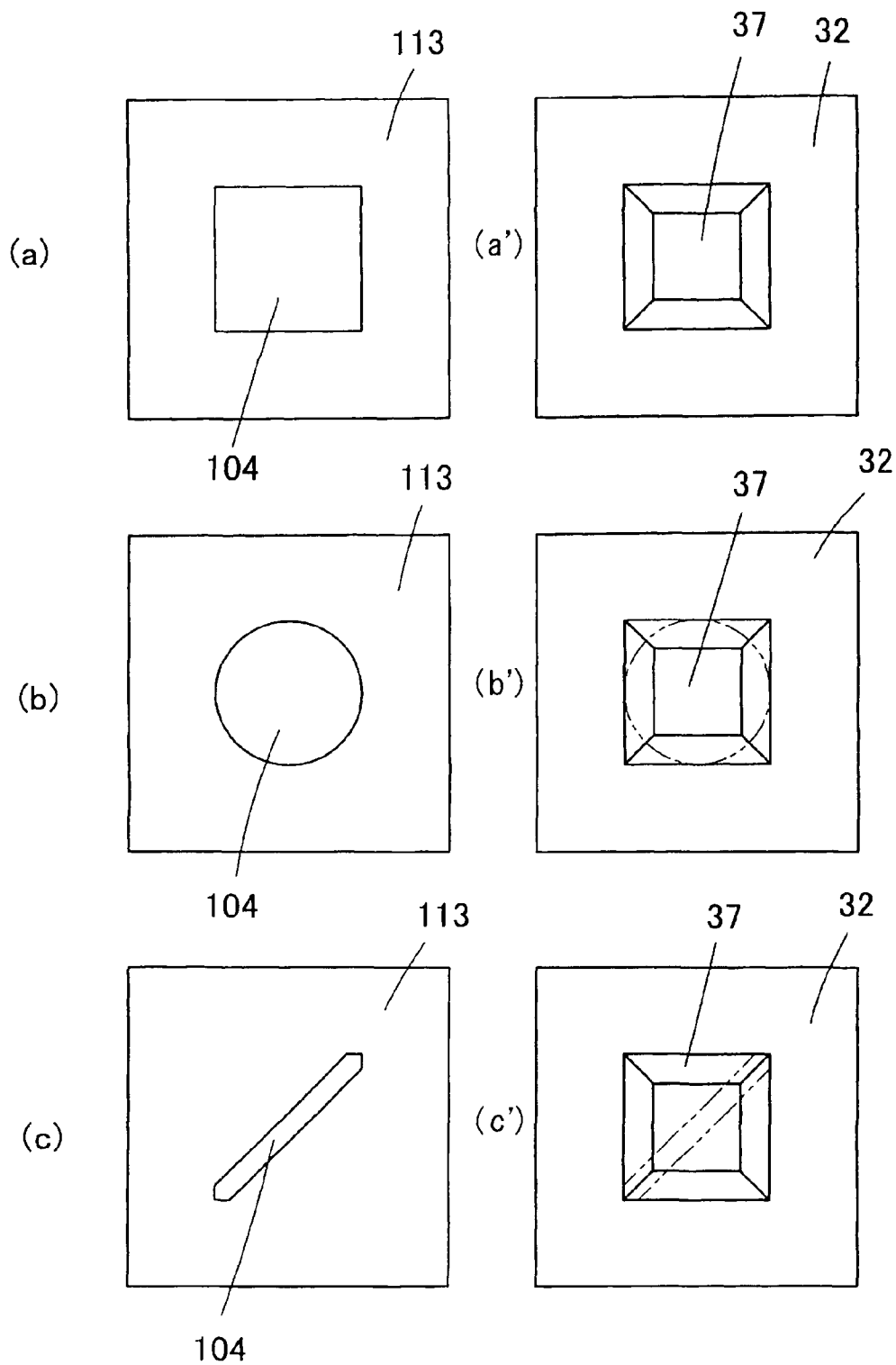

[Fig. 21]
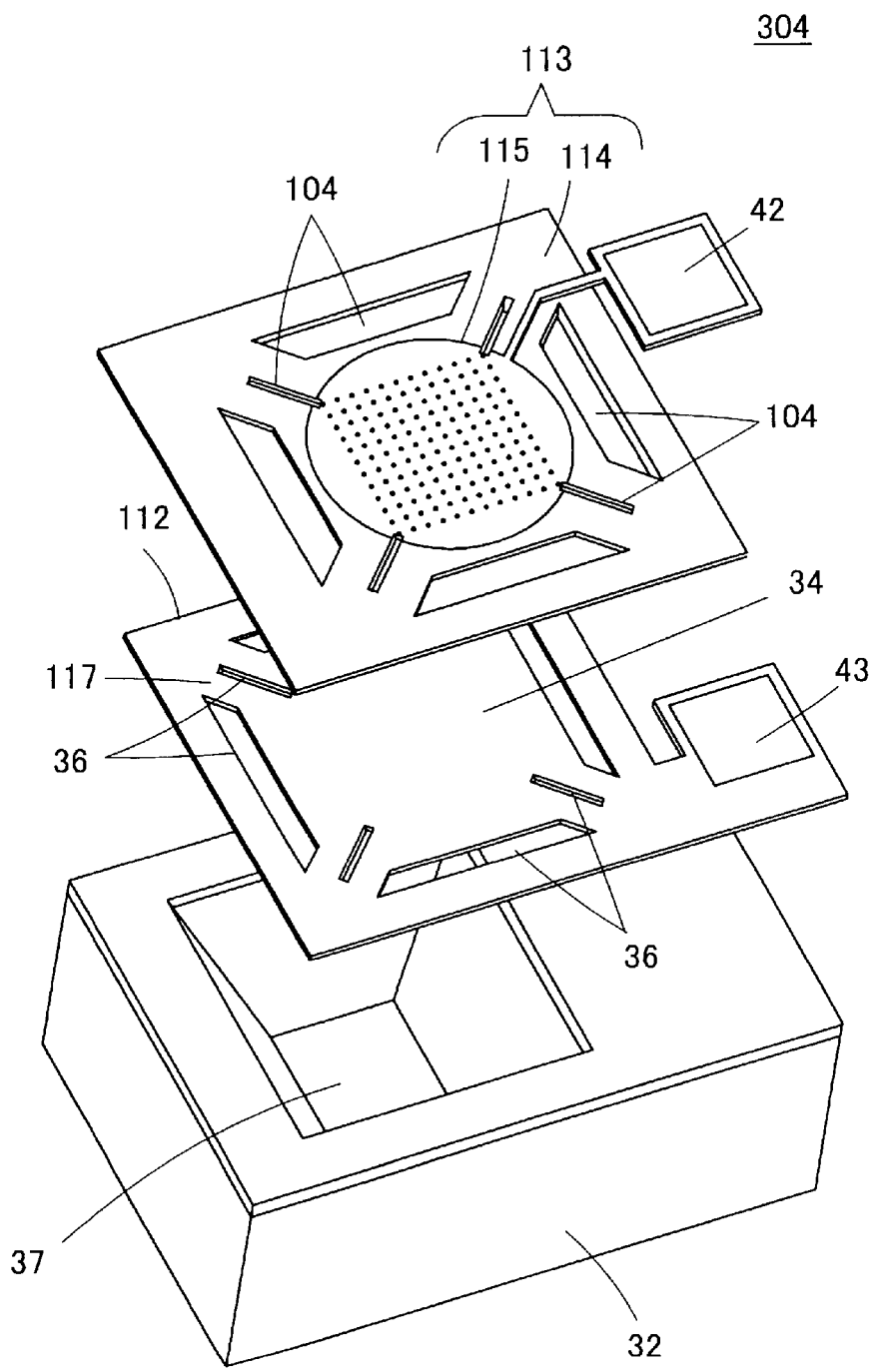

[Fig. 22]
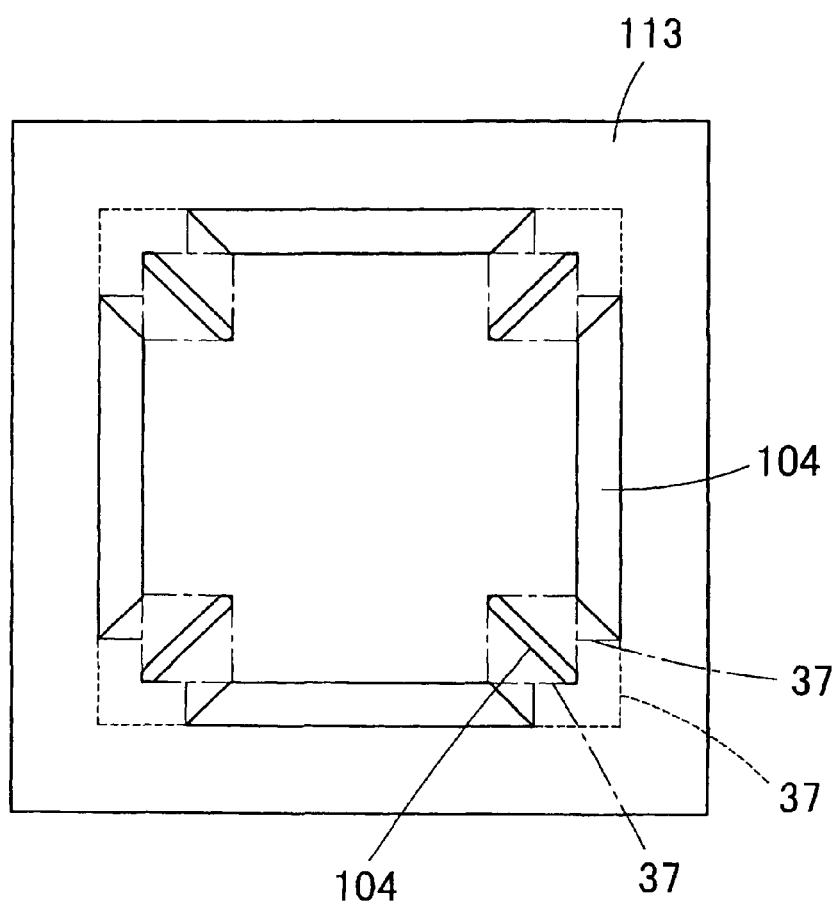

[Fig. 23]
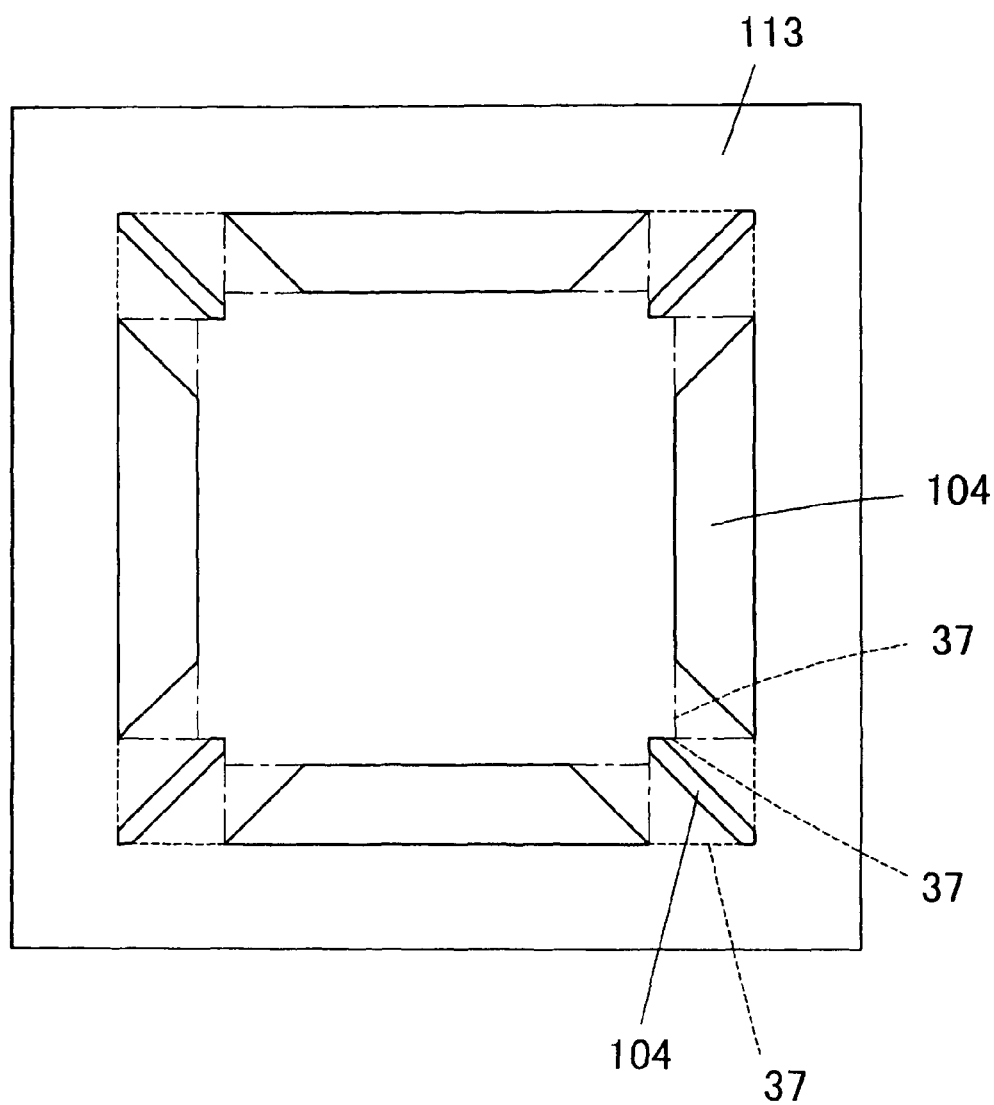

[Fig. 24]
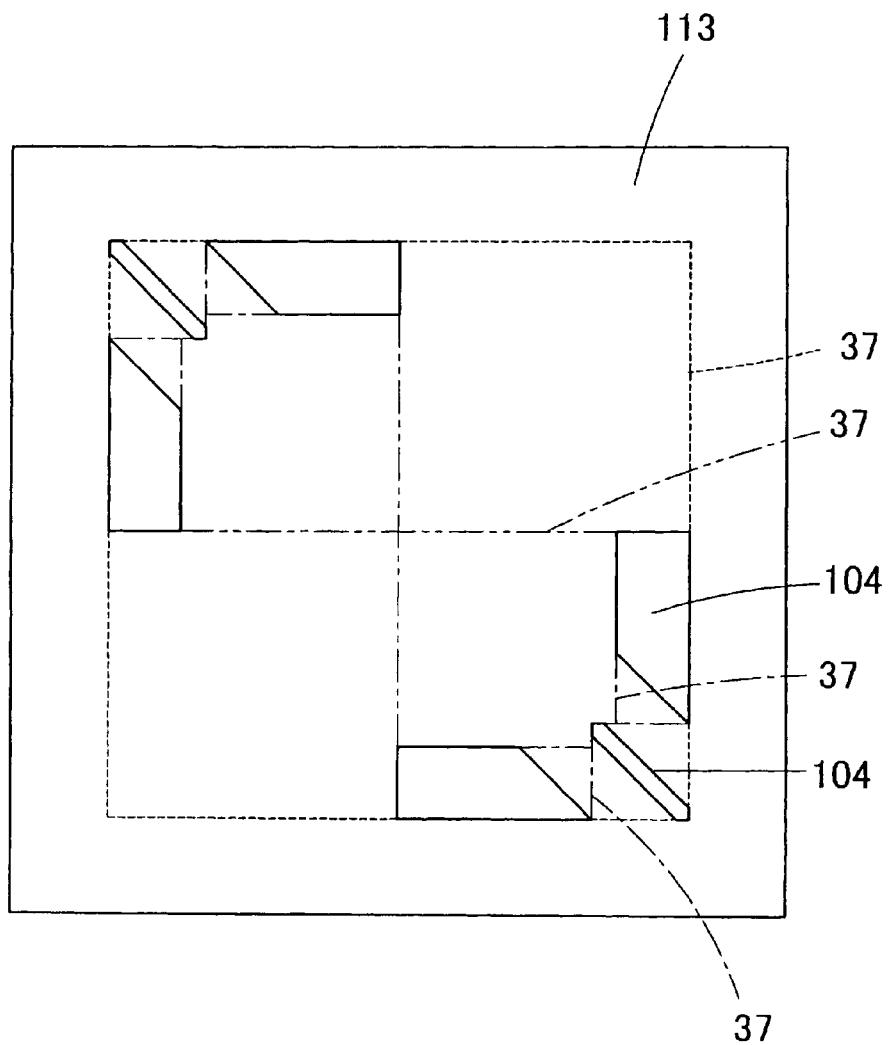

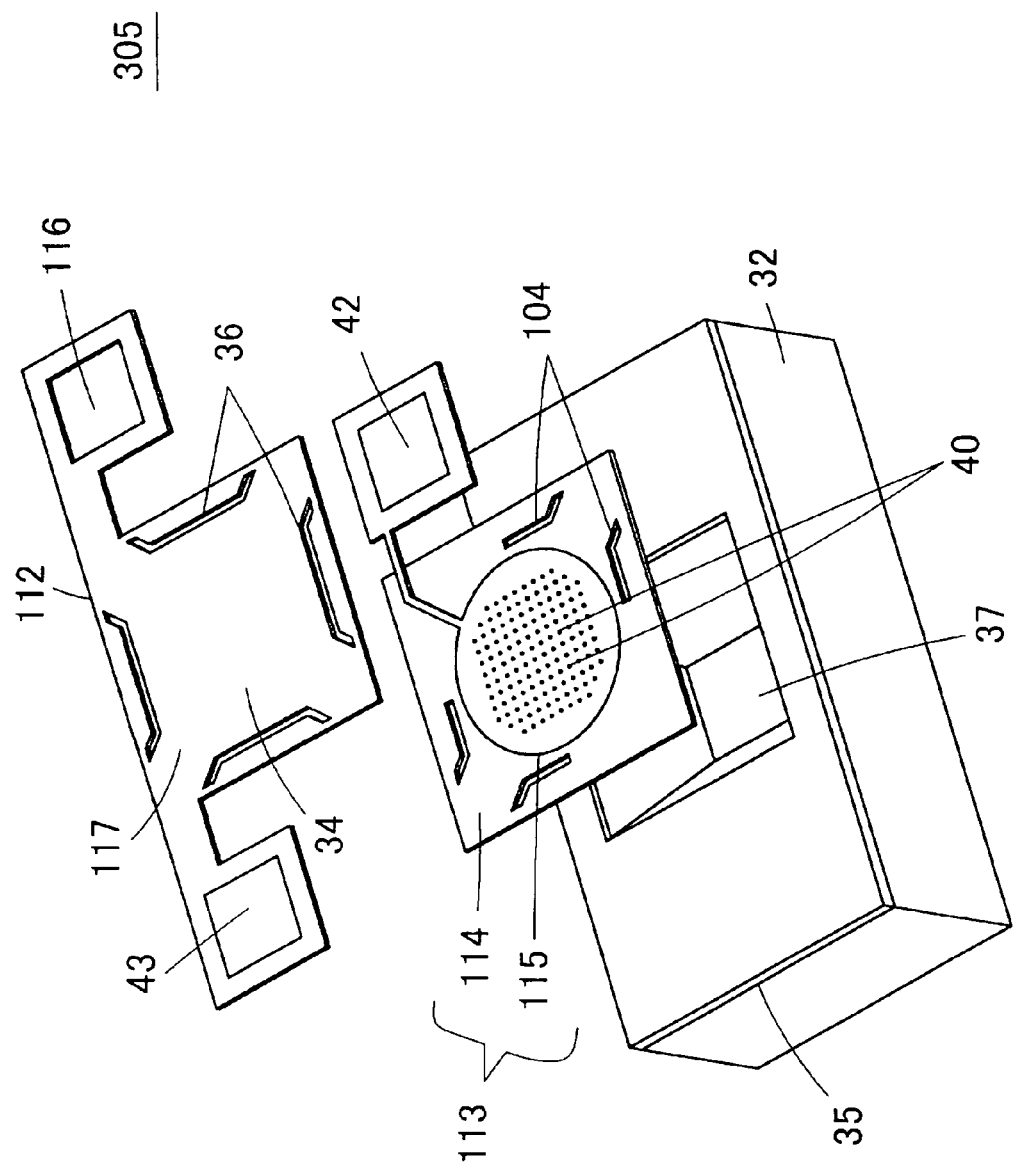
[Fig. 25]

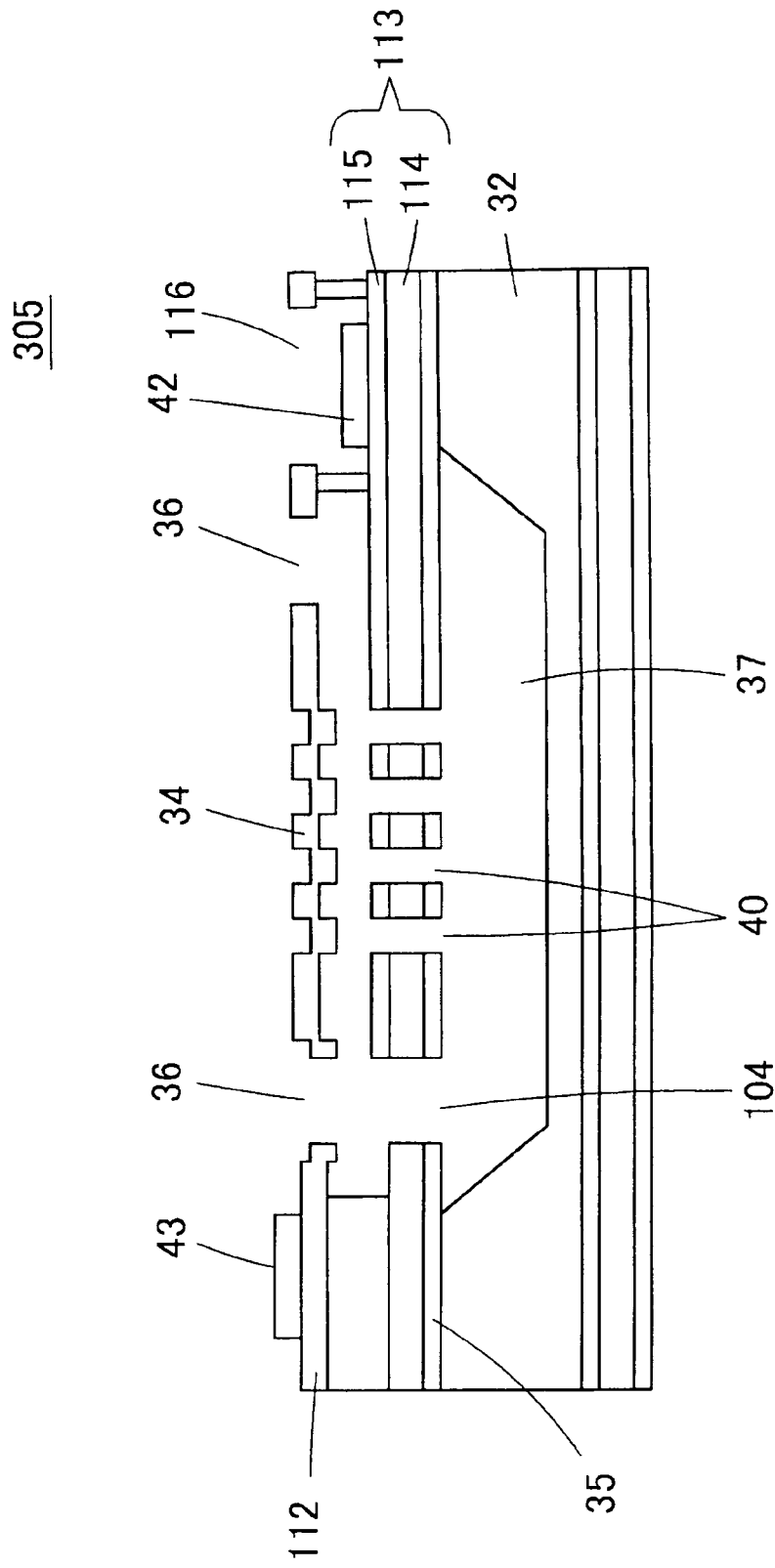
[Fig. 26]

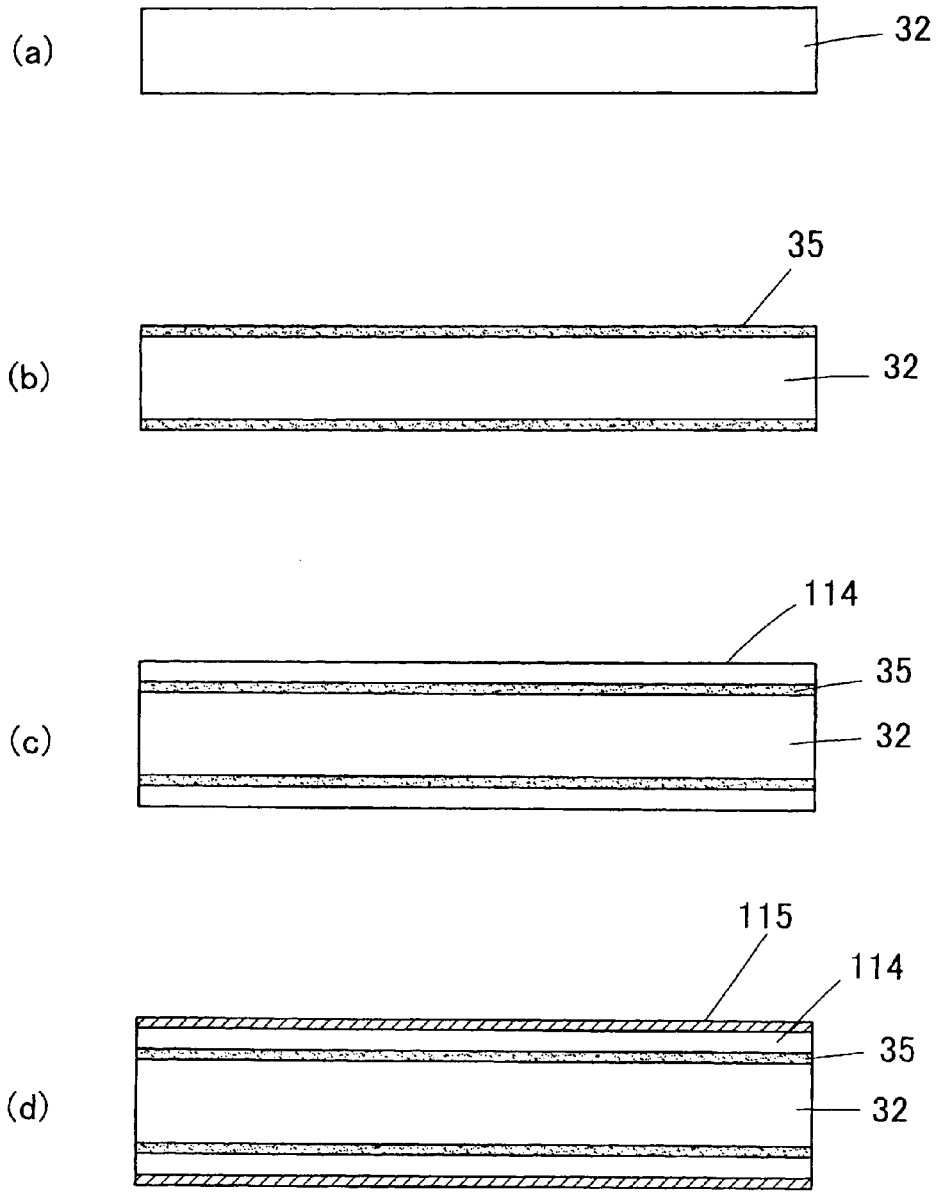
[Fig. 27]

[Fig. 28]
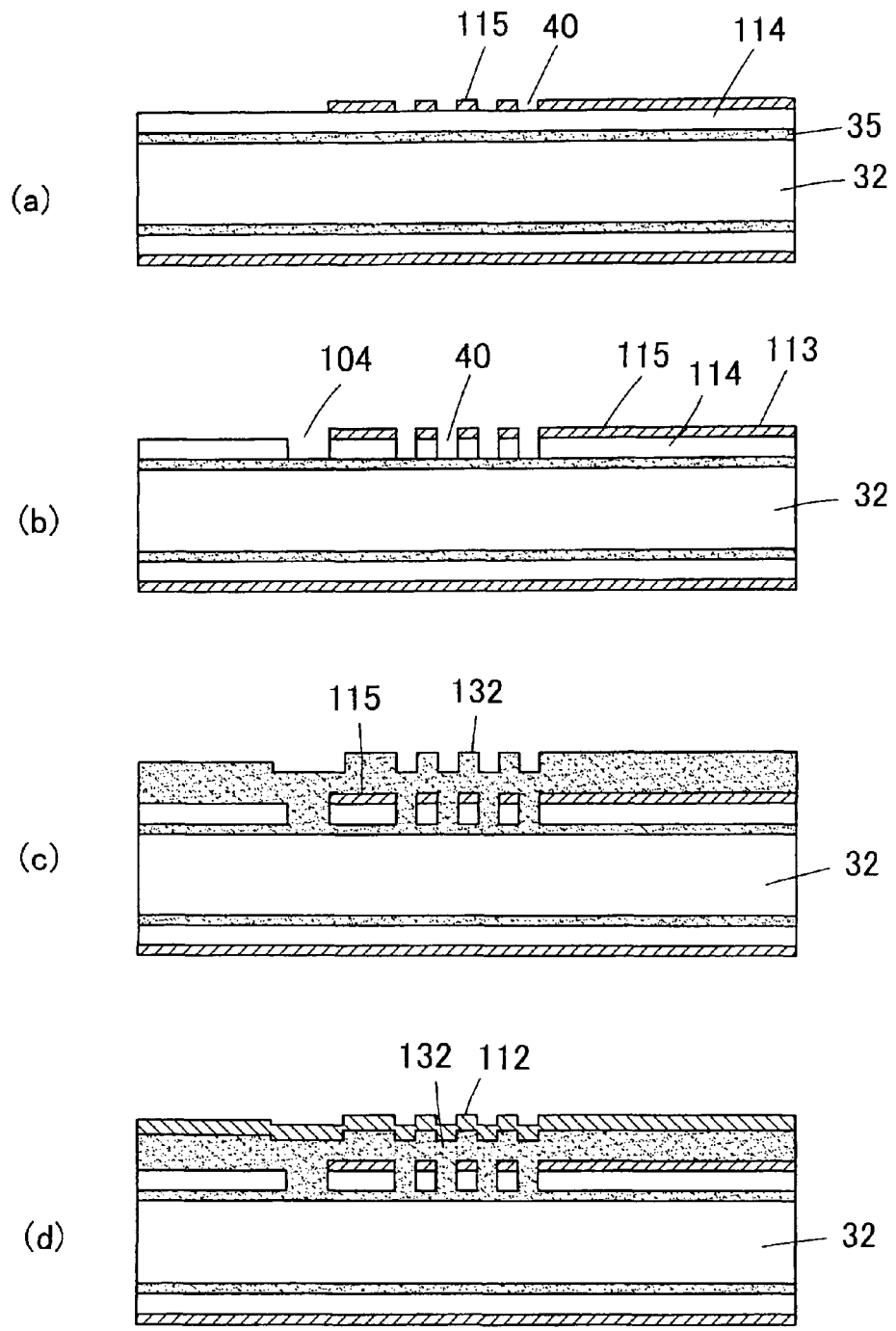

[Fig. 29]
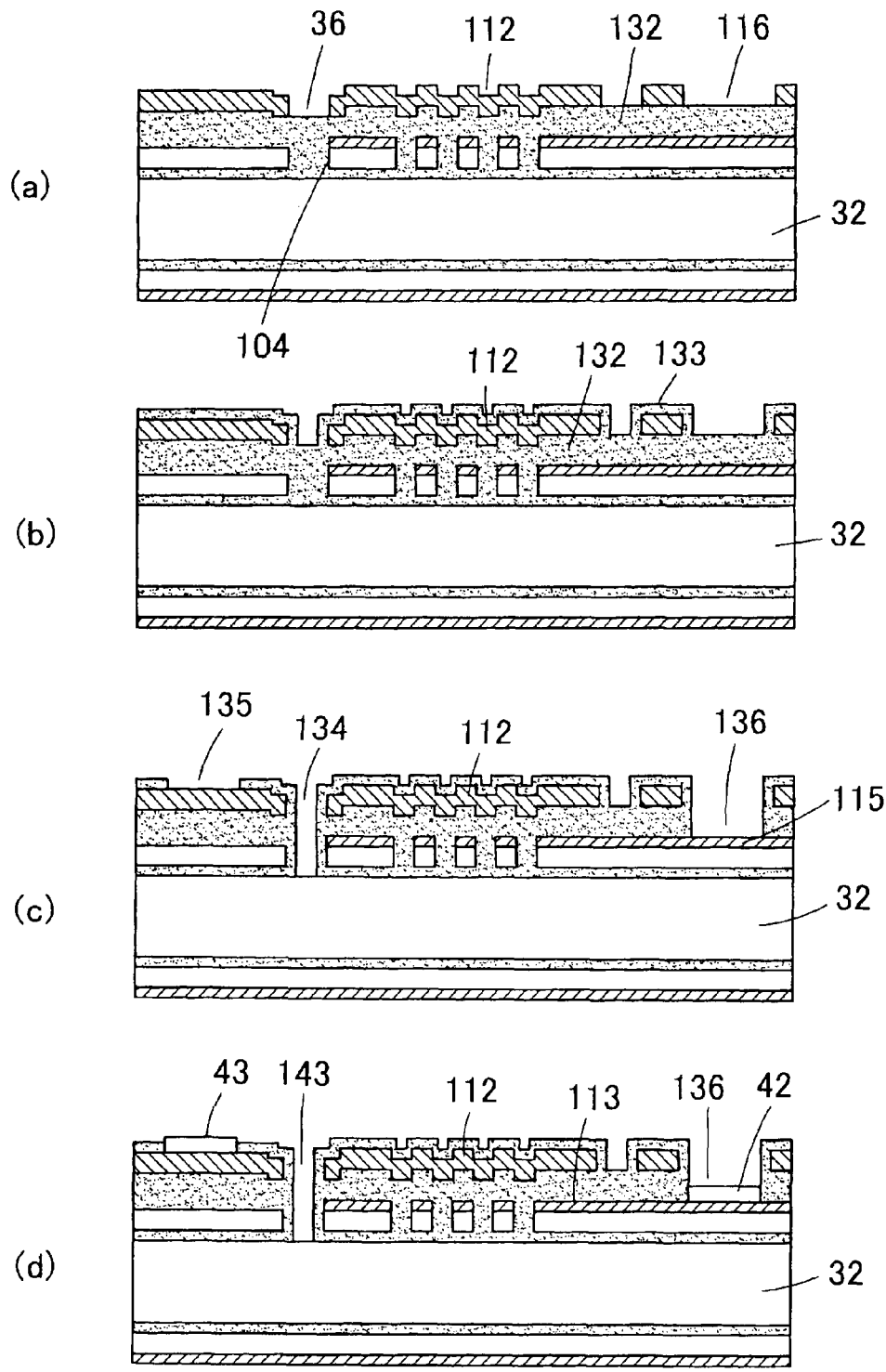

[Fig. 30]
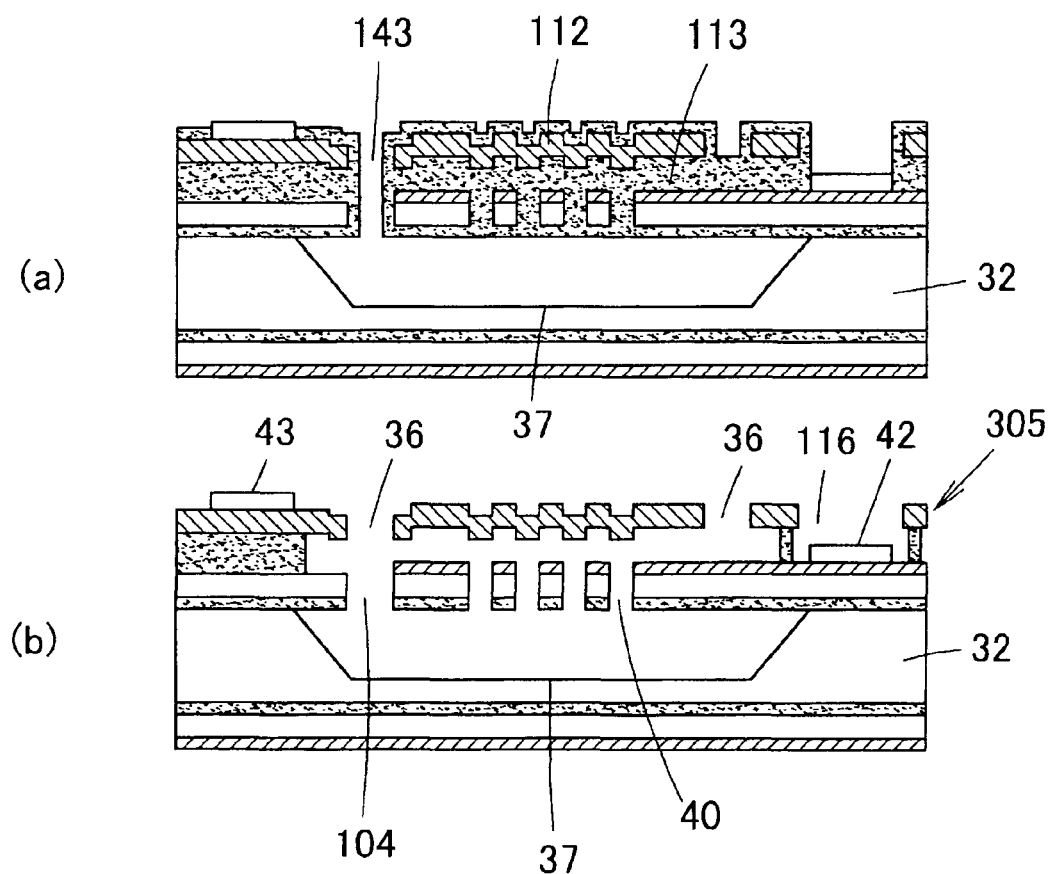

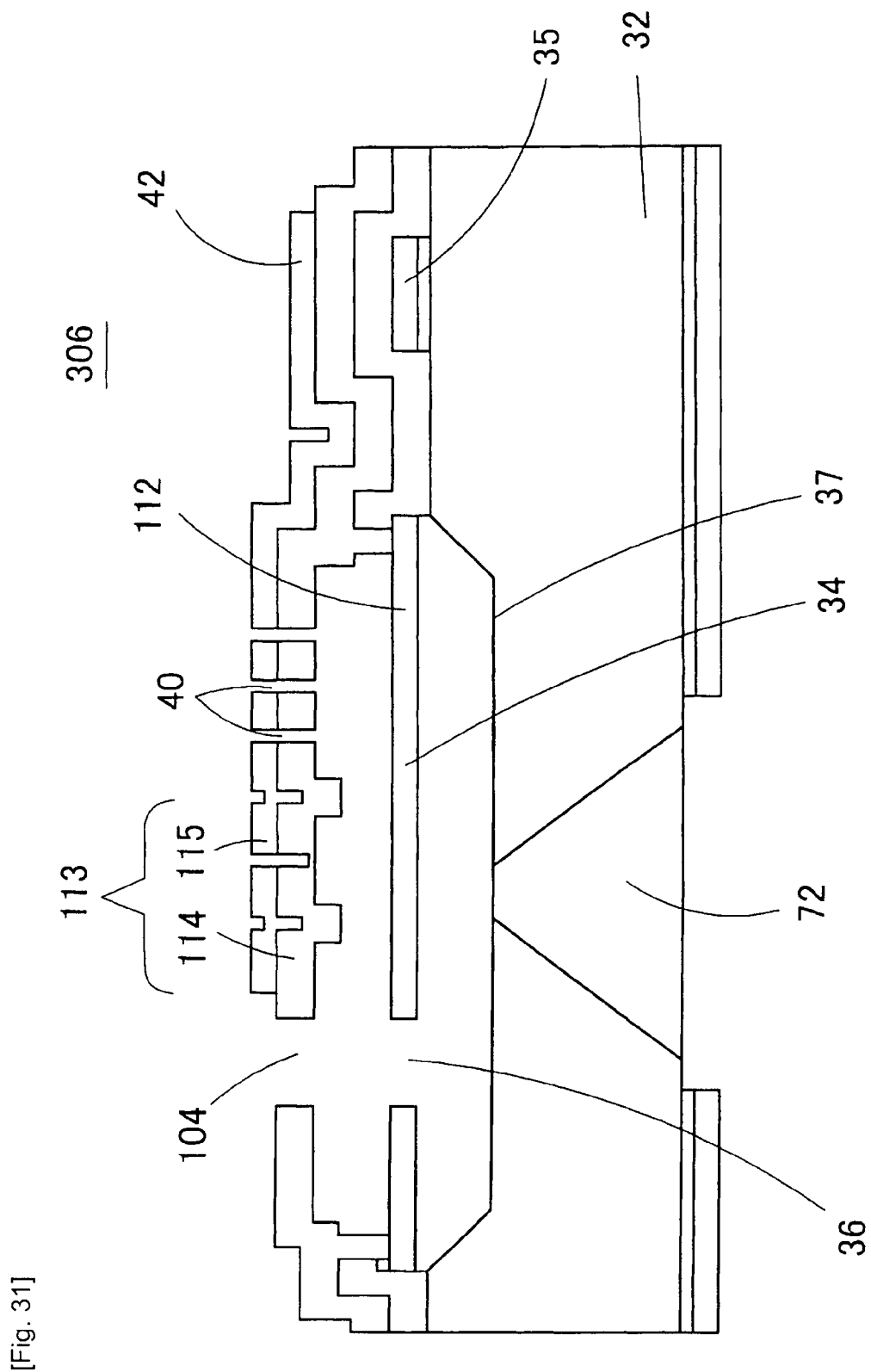
[Fig. 31]

[Fig. 32]
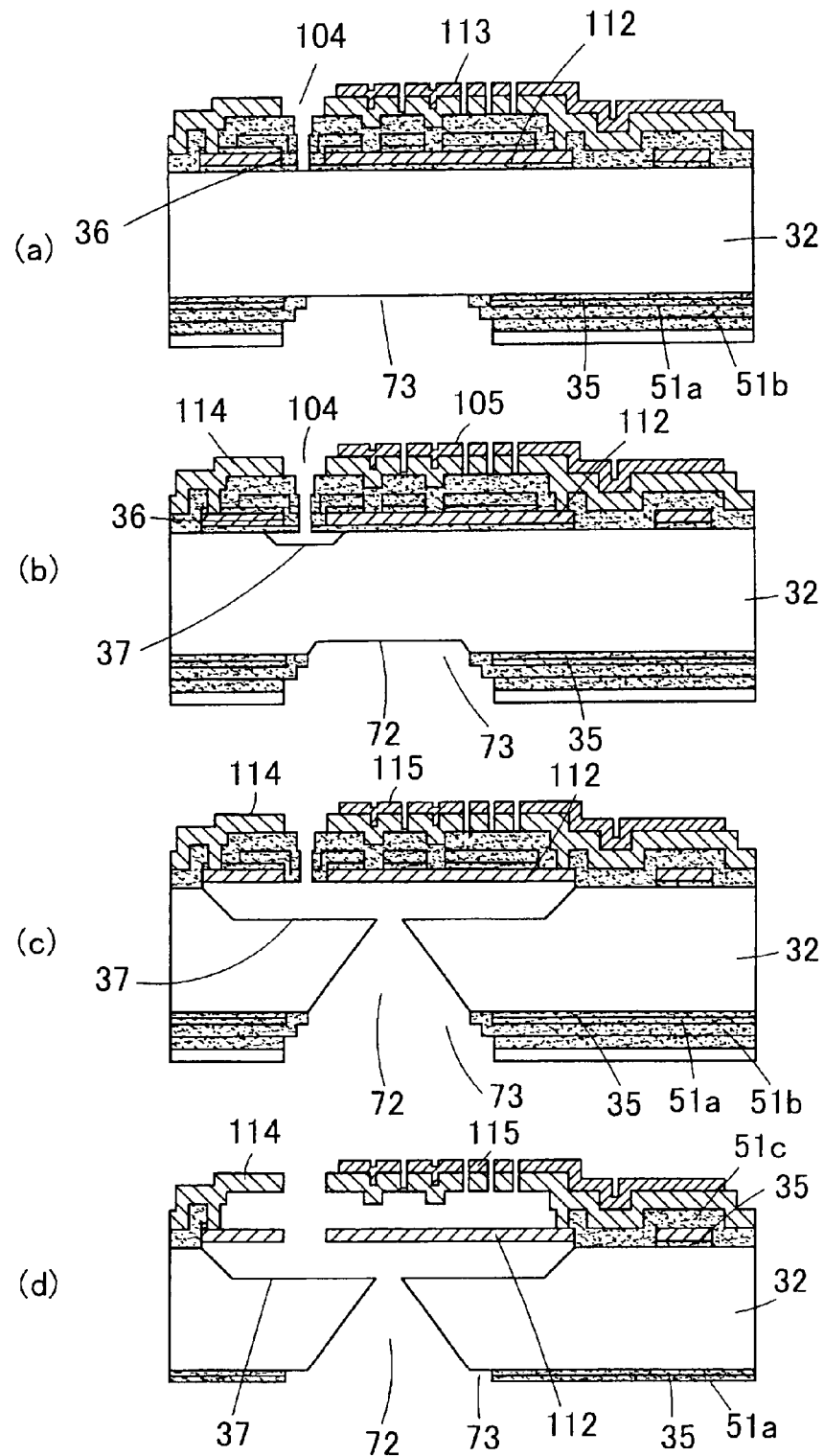

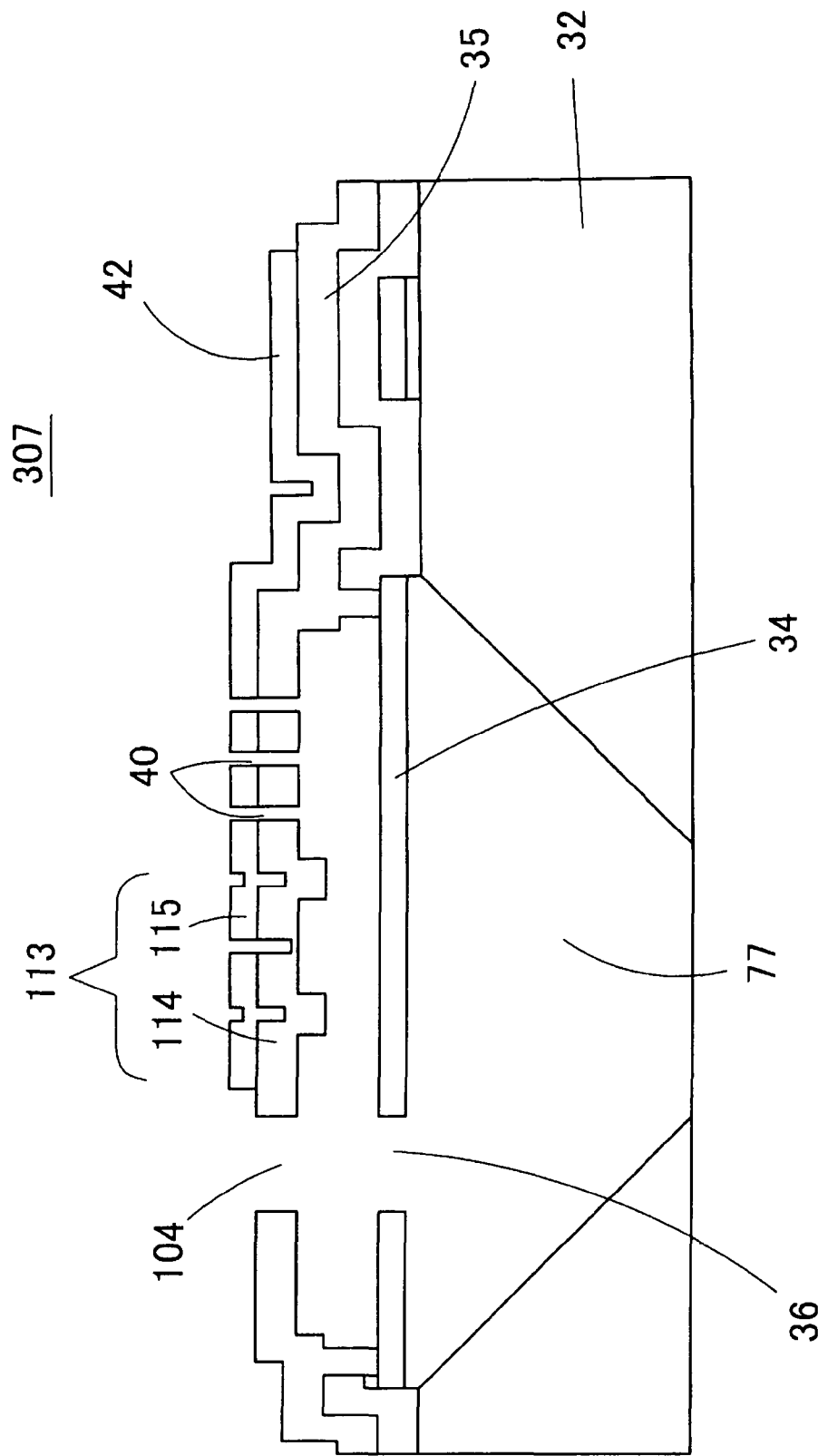
[Fig. 33]

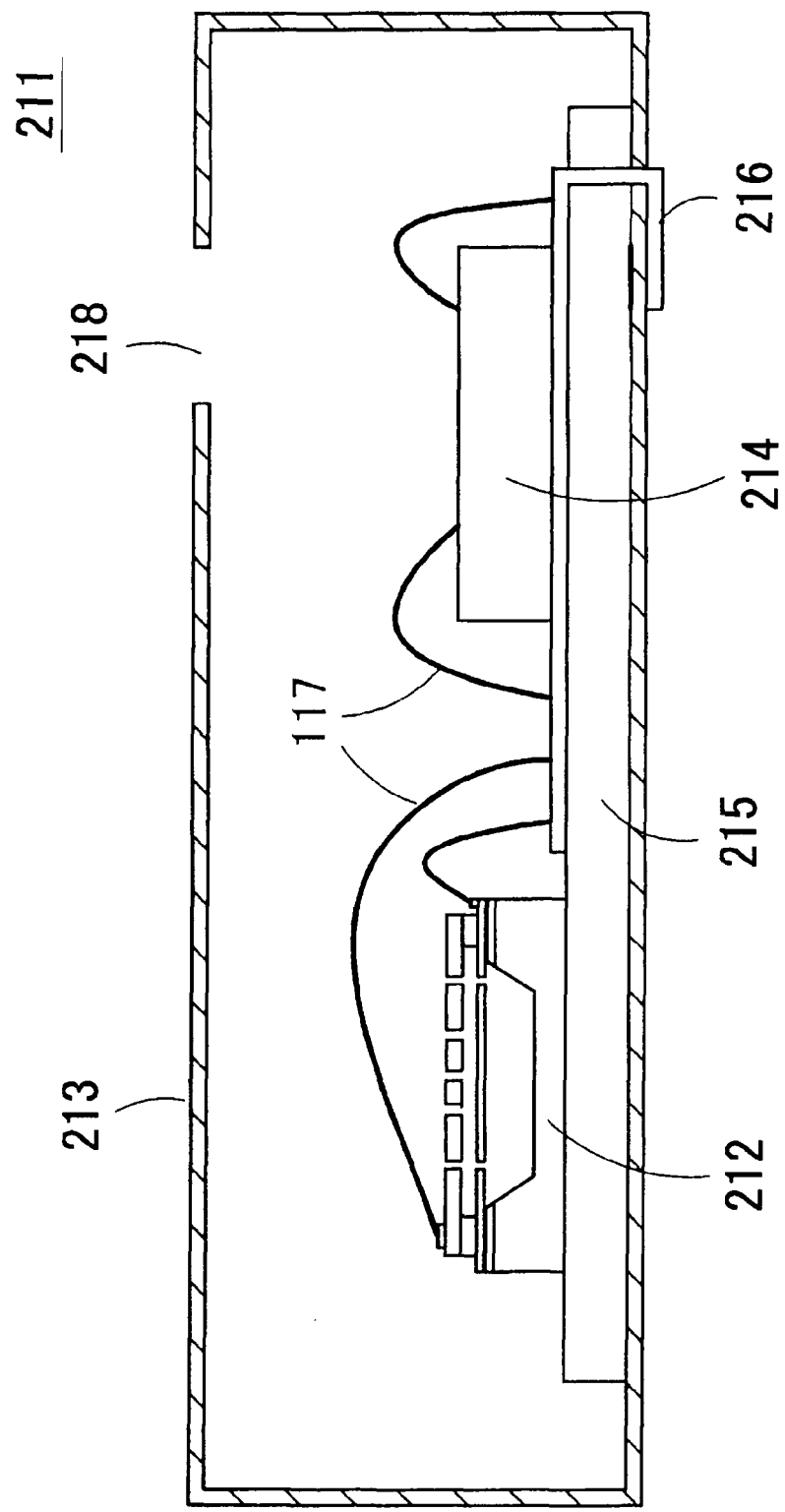
[Fig. 34]

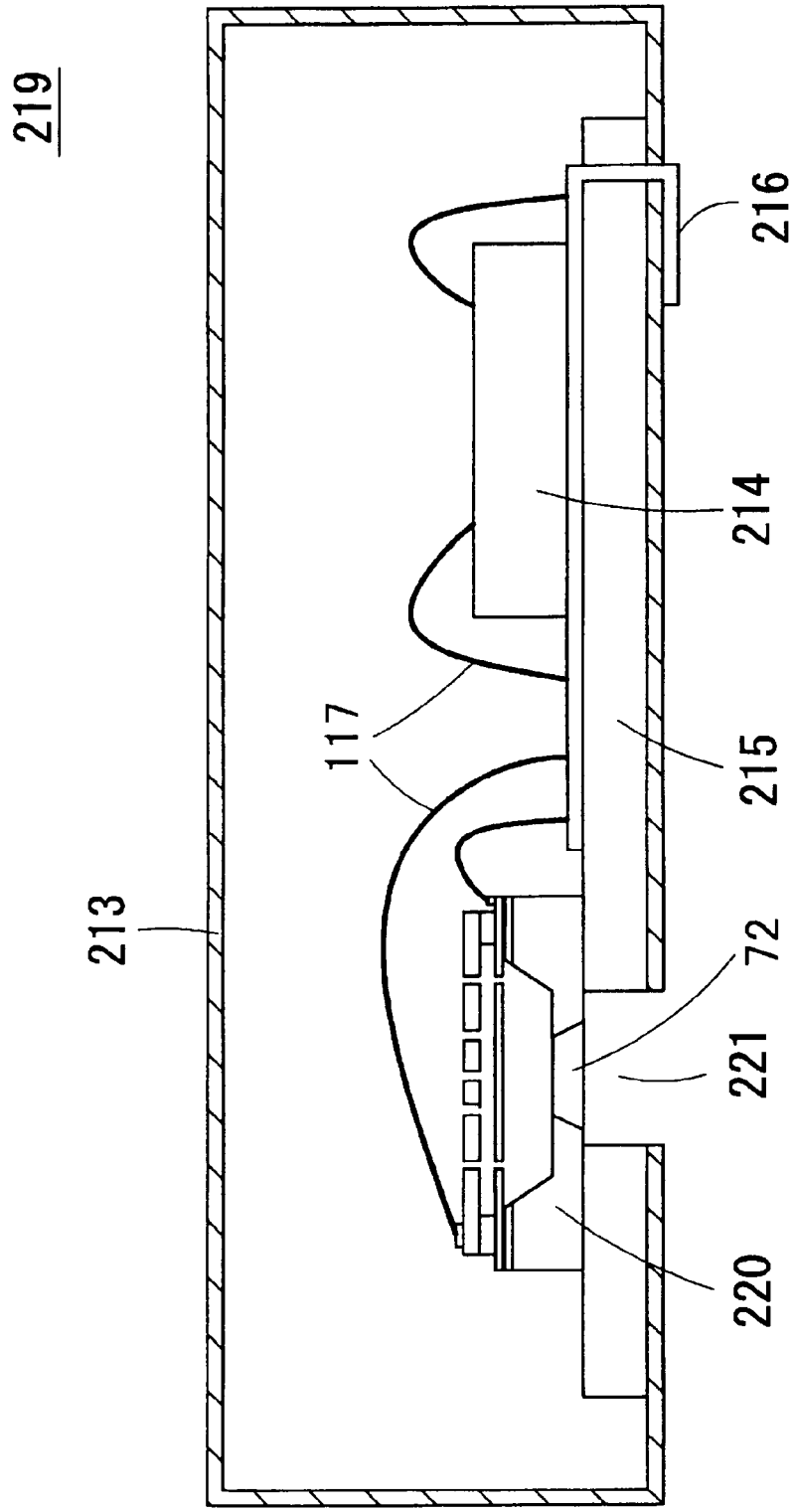
[Fig. 35]

[Fig. 36]
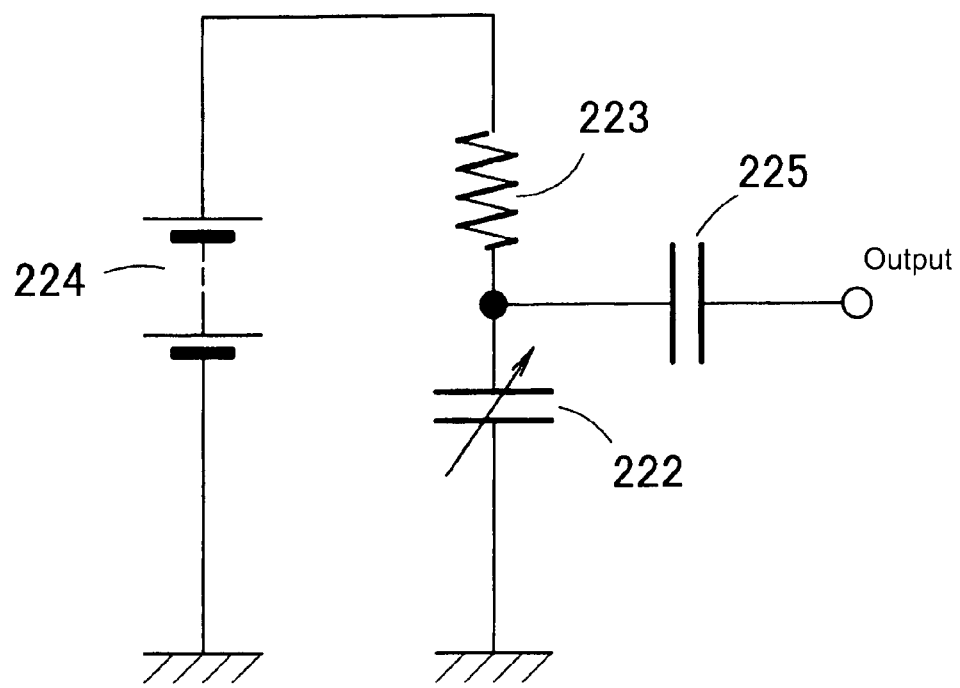

[Fig. 37]
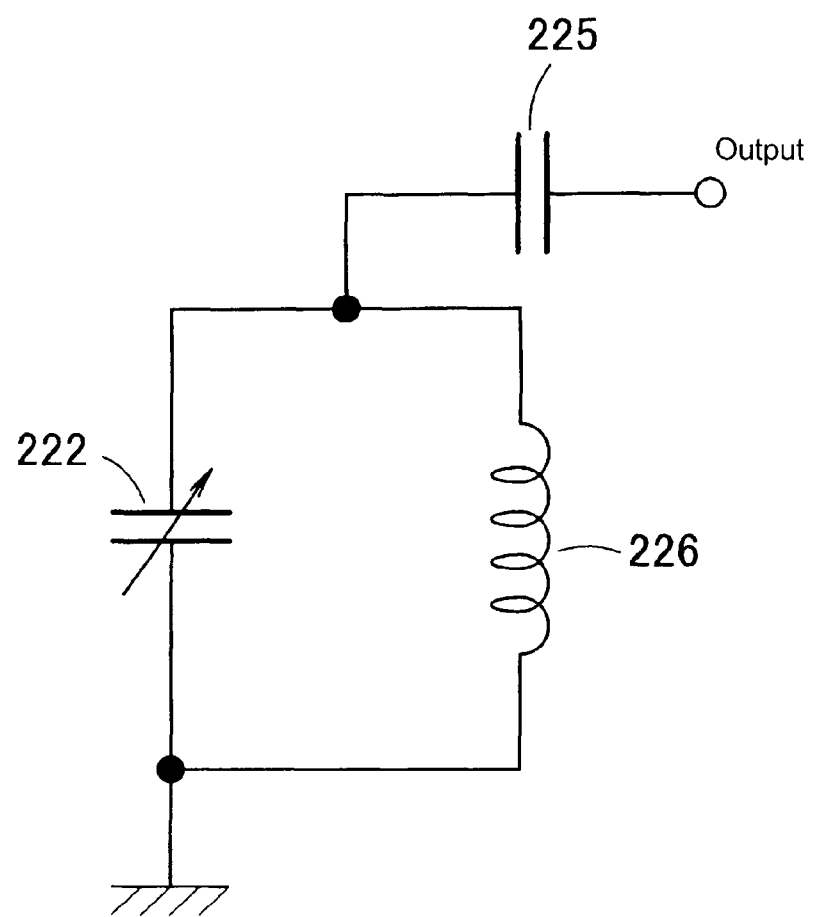

CAPACITIVE VIBRATION SENSOR AND METHOD FOR MANUFACTURING SAME

TECHNICAL FIELD

The present invention relates to a capacitive vibration sensor and a manufacturing method thereof, and more specifically, relates to a capacitive vibration sensor for detecting vibrations, such as a sound wave transmitted through a medium such as air and water, and a manufacturing method thereof.

BACKGROUND ART

FIGS. 1(a), 1(b) and 1(c) are views for explaining a general principle of a capacitor-type microphone which is one type of vibration sensors. A capacitor-type microphone 11 has a structure in which an opposing electrode plate 12 and a vibration electrode plate 13 are aligned face to face with each other with a small gap, with a dc voltage being applied between the two electrode plates 12 and 13 by a dc power supply 14. The opposing electrode plate 12 is allowed to have sufficient rigidity, or secured so as not to vibrate, and the vibration electrode plate 13 is made thinner in thickness so as to be vibrated by sound vibrations.

In this structure, when a sound vibration is transmitted to the capacitor-type microphone 11 as shown in FIG. 1(a), the thin vibration electrode plate 13 is vibrated by the sound vibration as shown in FIG. 1(b) to cause the electrostatic capacity between the opposing electrode plate 12 and the vibration electrode plate 13 to change. By electrically detecting the change in the electrostatic capacity, it is possible to extract sound (change in sound pressure) as shown in FIG. 1(c).

FIG. 2 is a cross-sectional view that shows a structure of a conventional capacitor-type microphone manufactured by utilizing a micro-machining technique. This capacitor-type microphone 21 has a structure in which: the upper face of a silicon substrate 22 having a through hole 27 opened in the center is covered with an insulating film 23, and a vibration electrode plate 24 is formed on the through hole 27, with an opposing electrode plate 26 being formed on the lower face of a perforated member 25 that covers the upper side of the vibration electrode plate 24. Thus, in the capacitor-type microphone 21, when a sound vibration is directed therein through the holes of the perforated member 25 and the opposing electrode plate 26 or through the through hole 27 in the lower face, to cause the vibration electrode plate 24 to vibrate, the electrostatic capacity between the vibration electrode plate 24 and the opposing electrode plate 26 is changed so that the sound vibration is outputted as a change in the electrostatic capacity.

In manufacturing processes of this capacitor-type microphone 21, after the insulating film 23, the vibration electrode plate 24 and the like have been formed on the upper face of the silicon substrate 22, the through hole 27 is opened by etching the silicon substrate 22 from the lower face side. With respect to the silicon substrate 22, in general, a (100) plane silicon wafer is used because it is easily available at a comparatively low price. For this reason, when the silicon substrate 22 is etched from the back face side, a plane having [111] orientation or an orientation equivalent to this, which is a dense plane of (100) plane silicon substrate, appears in the through hole 27 to cause a tilted face, with the result that the through hole 27 having a truncated pyramid shape is formed in the silicon substrate 22. Moreover, since the silicon substrate 22 is etched from the lower face side, the through hole 27 has a larger width on the lower face side of the silicon substrate 22 and a narrower width on the upper face side thereof.

For this reason, the opening area on the lower face side of the through hole 27 becomes larger than the area of the actual vibration portion of the vibration electrode plate 24 to cause the area of the silicon substrate 22 to become larger correspondingly. As a result, the conventional structure makes it difficult to miniaturize the capacitor-type microphone 21. Here, in the case when the thickness of the silicon substrate 22 is made thinner, although the opening area ratio between the upper face side and the lower face side of the through hole 27 becomes close to 1, there is a limitation in making the thickness of the silicon substrate 22 thinner from the viewpoint of the strength of the silicon substrate 22.

Moreover, Patent Document 1 has disclosed a piezo-resistor-type pressure sensor that detects a pressure of air or the like by converting a positional change of a thin film portion formed on a semiconductor substrate to a change in resistance value. In this piezo-resistor-type pressure sensor, in order to solve the above-mentioned problem caused by forming the thin film portion by etching the semiconductor substrate from the lower face side, the semiconductor substrate is etched from the upper face side to form a thin film portion. With this arrangement, after carrying out a film-forming process on the semiconductor substrate (silicon wafer) to form a thin film portion, an opening section is formed on a part of the thin film portion so that the silicon wafer is exposed, and an isotropic etching process is carried out through this opening section to provide a cavity in the semiconductor substrate so that the thin film portion is supported in a floating state from the upper face of the silicon substrate.

However, in the case of the microphone that is not used for measuring the absolute pressure of air, but is necessary to acquire sound as a smaller air pressure variation, the piezo resistor system composed of one thin film tends to cause problems with hysteresis and the like. For this reason, in general, an electrostatic capacitive system composed of two thin films is adopted. Even in this case, the structure having a rectangular shaped opening section or a square-frame-shaped opening section as disclosed in Patent Document 1 fails to form a thin film portion (vibration electrode plate) having superior sensitivity and frequency characteristics suitable for the microphone.

Patent Document 1: Japanese Patent Application Laid-Open No. 9-82983
Patent Document 2: Japanese Patent Application National Publication (Laid-Open) No. 2004-506394
Patent Document 3: Japanese Patent Application Laid-Open No. 2004-128957
Patent Document 4: Japanese Patent Application Laid-Open No. 2002-27595
Patent Document 5: Japanese Patent Application Laid-Open No. 62-284233
Patent Document 6: Japanese Patent Application National Publication (Laid-Open) No. 9-508777
Patent Document 7: Japanese Patent Application Laid-Open No. 2001-13156

DISCLOSURE OF THE INVENTION

Problems to be Solved by the Invention

The present invention relates to a capacitive vibration sensor constituted by a vibration electrode plate and an opposing electrode plate, and its objective is to further miniaturize the capacitive vibration sensor to be manufactured by utilizing a micromachining technique, without causing degradation in the sensitivity and frequency characteristics, by etching the semiconductor substrate from the side on which the two electrode plates are formed.

Means for Solving the Problems

A capacitive vibration sensor in accordance with the present invention, which is provided with a vibration electrode plate and an opposing electrode plate that are aligned face to face with each other and placed on a surface of a semiconductor substrate so as to cover a space formed in the semiconductor substrate, is characterized by a structure in which: a plurality of etching holes are opened through the vibration electrode plate, and a part of the vibration electrode plate is separated apart from the semiconductor substrate, with a holding portion being left, by the etching holes of the vibration electrode plate, so that a diaphragm is formed; etching holes are opened on the opposing electrode plate in such a manner that each etching hole is overlapped with each of the etching holes of the vibration electrode plate, with adjacent rectangles, each circumscribing the etching hole, of the opposing electrode plate being made in contact with each other or overlapped with each other, when viewed in a direction perpendicular to the surface of the semiconductor substrate; and the space of the semiconductor substrate is formed by carrying out an etching process from the surface side of each of the two electrode plates to the opposite side of each of the two electrode plates through each of the etching holes of the opposing electrode plate and the vibration electrode plate.

In the capacitive vibration sensor in accordance with the present invention, a space (for example, a through hole and a concave section) is formed in a semiconductor substrate by etching the semiconductor substrate from the surface side of the two electrode plates to the surface side opposite to the two electrode plates so that the capacitive vibration sensor can be miniaturized in comparison with the prior art structure.

Moreover, as the capacitive vibration sensor is miniaturized, the vibration electrode plate is also made smaller; however, the miniaturized vibration electrode plate causes an excessively high resonance frequency, resulting in a reduction in the sensitivity to sound. In contrast, when the etching hole is opened through the vibration electrode plate, the rigidity is made lower so that the resonance frequency can be made lower, with the detection sensitivity of the capacitive vibration sensor being improved. Furthermore, in the case when the space in the semiconductor substrate is prepared as a concave section with one side being closed, air is enclosed in the space to serve as an air dumper, with the result that the sensitivity of the vibration electrode plate is lowered; however, since the etching hole is opened through the vibration electrode plate, the air in the space can be released so that the detection sensitivity of the capacitive vibration sensor can be improved. Moreover, by opening the etching hole in the vibration electrode plate, it is possible to restrain variations in the sensor sensitivity and the possibility of damages due to temperature changes.

In accordance with another aspect of the capacitive vibration sensor of the present invention, since the vibration electrode plate is separated apart from the silicon substrate by the etching holes of the vibration electrode plate, with a holding portion being left, the effective vibration area of the vibration electrode plate is increased so that the sensitivity of the capacitive vibration sensor can be improved. Moreover, since the etching holes, provided on the opposing electrode plate, are opened in such a manner that circumscribing rectangles are made in contact with each other, or overlapped with each other, the spaces formed in the semiconductor substrate by the respective etching holes are connected to one another to finally form a large space. Therefore, the etching hole in the opposing electrode plate can be made smaller so that the opposing electrode plate is made to hardly vibrate in response to vibrations of sound waves or the like.

In accordance with one preferred mode of the capacitive vibration sensor of the present invention, the etching hole of the opposing electrode plate is formed into a slit shape. With this mode, since the etching hole of the opposing electrode plate is allowed to have the slit shape, the resistance of a fluid passing through the etching hole of the opposing electrode plate becomes greater, making it possible to improve the low frequency characteristics of the capacitive vibration sensor.

In accordance with another preferred mode of the capacitive vibration sensor of the present invention, the area of each etching hole on the opposing electrode plate is set to ½ of the area of each etching hole on the vibration electrode plate. With this mode, since the area of each etching hole on the opposing electrode plate is set to a half of the area of each etching hole on the vibration electrode plate, the resistance of a fluid passing through the etching hole of the opposing electrode plate becomes greater, making it possible to improve the low frequency characteristics of the capacitive vibration sensor. Moreover, the rigidity of the vibration electrode plate is enhanced so that the durability of the capacitive vibration sensor can be improved.

In accordance with still another preferred mode of the capacitive vibration sensor of the present invention, the etching holes of the vibration electrode plate are formed in the center of four sides in a vibration area of the vibration electrode plate, with each of the edges being formed into an arc shape. With this mode, since the holding portions of the vibration electrode plate to be formed among the etching holes are positioned on four corners of the vibration area of the vibration electrode plate, a stress concentration hardly occurs in the holding portion, thereby making it possible to improve the durability of the capacitive vibration sensor.

In accordance with still another preferred mode of the semiconductor substrate in the capacitive vibration sensor of the present invention, a through hole that communicates with the space is formed in the semiconductor substrate on the side opposite to the two electrode plates. With this mode, since the space of the semiconductor substrate is allowed to penetrate the semiconductor substrate, not only vibrations of sound waves or the like transmitted to the semiconductor substrate from the side on which the two electrode plates are provided, but also vibrations transmitted thereto from the side opposite to the two electrode plates can be detected so that vibrations can be detected on both of the surfaces.

A microphone relating to the present invention is provided with the capacitive vibration sensor according to the present invention, and an output circuit that converts a sound signal detected by the capacitive vibration sensor to an electric signal and outputs the resulting signal.

An acoustic transducer relating to the present invention is provided with the capacitive vibration sensor according to the present invention, an output circuit that converts a sound signal detected by the capacitive vibration sensor to an electric signal and outputs the resulting signal, and an input circuit that inputs the electric signal to the capacitive vibration sensor to generate sound vibrations.

In accordance with the microphone and the acoustic transducer of the present invention, since the capacitive vibration sensor can be miniaturized, it becomes possible to achieve a small size and light weight of a microphone and an acoustic transducer.

A method of manufacturing a capacitive vibration sensor in accordance with the present invention, which relates to the capacitive vibration sensor having a vibration electrode plate and an opposing electrode plate that are made face to face with each other and placed on a surface of a semiconductor substrate so as to cover a space formed in the semiconductor substrate, is provided with the steps of: forming the vibration electrode plate having etching holes above the semiconductor substrate so as to cover the surface of the semiconductor substrate; forming the opposing electrode plate above the vibration electrode plate with a sacrifice layer interposed in between; opening a plurality of etching holes on the opposing electrode plate in such a manner that each etching hole is overlapped with each of the etching holes of the vibration electrode plate, with adjacent circumscribing rectangles are made in contact with each other or overlapped with each other; forming the space in the semiconductor substrate by wet etching or dry etching the semiconductor substrate through each of the etching holes of the opposing electrode plate and the vibration electrode plate; and after forming the space, removing the sacrifice layer interposed between the vibration electrode film and the opposing electrode film.

In accordance with the method of manufacturing a capacitive vibration sensor of the present invention, etching holes are preliminarily provided in the vibration electrode plate and the opposing electrode plate, and an etching solution is made in contact with the semiconductor substrate through the etching holes so as to carry out a wet etching process, or a gas is made in contact therewith through the etching holes so as to carry out a dry etching process so that a space can be formed in the semiconductor substrate from the side of the vibration electrode plate and the opposing electrode plate. As a result, a capacitive vibration sensor, thus manufactured, can be miniaturized. Moreover, since the etching holes in the vibration electrode plate are allowed to remain as holes, it becomes possible to lower the resonance frequency of the vibration electrode plate, and consequently to improve the detection sensitivity of the capacitive vibration sensor.

Here, the constituent elements as described above can be desirably combined on demand.

BRIEF DESCRIPTIONS OF THE DRAWINGS

FIGS. 1(a), 1(b) and 1(c) are views for explaining a general principle of a capacitor-type microphone which is one kind of vibration sensors.

FIG. 2 is a cross-sectional view that shows a structure of a conventional capacitor-type microphone manufactured by utilizing a micromachining technique.

FIG. 3 is a schematic exploded perspective view that shows a capacitive vibration sensor in accordance with embodiment 1 of the present invention.

FIG. 4 is a plan view that shows the capacitive vibration sensor of embodiment 1.

FIG. 5 is a cross-sectional view that shows the capacitive vibration sensor of embodiment 1.

FIG. 6(a) is a plan view that shows an opposing electrode plate forming a constituent part of the capacitive vibration sensor of embodiment 1; FIG. 6(b) is a plan view that shows a vibration electrode plate forming a constituent part of the capacitive vibration sensor of embodiment 1; and FIG. 6(c) is a plan view that shows a silicon substrate forming a constituent part of the capacitive vibration sensor of embodiment 1.

FIG. 7 is a view that indicates an application area of a capacitive vibration sensor when a vibration electrode plate having a small holding portion is used and an application area of a capacitive vibration sensor when a vibration electrode plate having a large holding portion is used.

FIGS. 8(a) to 8(d) are cross-sectional views that schematically show processes in which the capacitive vibration sensor of embodiment 1 is manufactured by using a micromachining technique.

FIGS. 9(a) to 9(d) are cross-sectional views that schematically show manufacturing processes following the process of FIG. 8(d).

FIGS. 10(a) to 10(d) are cross-sectional views that schematically show manufacturing processes following the process of FIG. 9(d).

FIGS. 11(a) to 11(d) are cross-sectional views that schematically show manufacturing processes following the process of FIG. 10(d).

FIGS. 12(a) to 12(c) and FIGS. 12(a') to 12(c') are schematic plan views and cross-sectional views that respectively show states in which a silicon substrate is gradually etched through etching holes of an opposing electrode plate.

FIGS. 13(a) and 13(b) are plan views that schematically show the state after the process of FIG. 12(c); and FIGS. 13(a') and 13(b') are cross-sectional views that schematically show the state after the process of FIG. 12(c').

FIG. 14 is a view that explains a modified example of the manufacturing process of the capacitive sensor of embodiment 1.

FIG. 15 is a view that explains another modified example of the manufacturing process of the capacitive sensor of embodiment 1.

FIG. 16(a) is a plan view that shows an opposing electrode plate forming a constituent part of a capacitive vibration sensor in accordance with embodiment 2 of the present invention; and FIG. 16(b) is a plan view that shows a vibration electrode plate forming a constituent part of the capacitive vibration sensor in accordance with embodiment 2 of the present invention.

FIG. 17(a) is a plan view that shows an opposing electrode plate forming a constituent part of a capacitive vibration sensor in accordance with embodiment 3 of the present invention; and FIG. 17(b) is a plan view that shows a vibration electrode plate forming a constituent part of the capacitive vibration sensor in accordance with embodiment 3 of the present invention.

FIGS. 18(a) to 18(d) and FIGS. 18(a') to 18(d') are schematic plan views and cross-sectional views that respectively show states in which in manufacturing processes of the capacitive vibration sensor of embodiment 3, a silicon substrate is gradually etched.

FIG. 19(a) is a plan view that shows an opposing electrode plate of the capacitive vibration sensor of a modified example of embodiment 3; and FIG. 19(b) is a plan view that shows a vibration electrode plate of the modified example of embodiment 3.

FIGS. 20(a) to 20(c) are plan views that show etching holes having various shapes of the capacitive vibration sensor; and FIGS. 20(a') to 20(c') are plan views that show shapes of concave sections formed on a silicon substrate by the respective etching holes of FIGS. 20(a) and 20(c).

FIG. 21 is an exploded perspective view that schematically shows a capacitive vibration sensor in accordance with embodiment 4 of the present invention.

FIG. 22 is a view that explains a state in which a silicon substrate is etched in manufacturing processes of the capacitive vibration sensor in accordance with embodiment 4.

FIG. 23 is a view that explains a state in which a silicon substrate is etched in manufacturing processes of the capacitive vibration sensor in accordance with a modified example of embodiment 4.

FIG. 24 is a view that shows a state in which a silicon substrate is etched in manufacturing processes of a capacitive vibration sensor in accordance with another modified example of embodiment 4.

FIG. 25 is an exploded perspective view that schematically shows a capacitive vibration sensor in accordance with embodiment 5.

FIG. 26 is a cross-sectional view of the capacitive vibration sensor in accordance with embodiment 5.

FIGS. 27(a) to 27(d) are cross-sectional views that explain manufacturing processes of the capacitive vibration sensor in accordance with embodiment 5.

FIGS. 28(a) to 28(d) are cross-sectional views that explain manufacturing processes of the capacitive vibration sensor in accordance with embodiment 5, which correspond to the processes following the process of FIG. 27(d).

FIGS. 29(a) to 29(d) are cross-sectional views that explain manufacturing processes of the capacitive vibration sensor in accordance with embodiment 5, which correspond to the processes following the process of FIG. 28(d).

FIGS. 30(a) to 30(b) are cross-sectional views that explain manufacturing processes of the capacitive vibration sensor in accordance with embodiment 5, which correspond to the processes following the process of FIG. 29(d).

FIG. 31 is a cross-sectional view showing a structure of a capacitive vibration sensor in accordance with embodiment 6.

FIGS. 32(a) to 32(d) are cross-sectional views that schematically show a part of manufacturing processes of the capacitive vibration sensor in accordance with embodiment 6.

FIG. 33 is a cross-sectional view that shows a modified example of embodiment 6 of the present invention.

FIG. 34 is a cross-sectional view that shows a capacitor-type microphone in which a capacitive vibration sensor is housed in a case.

FIG. 35 is a cross-sectional view that shows another capacitor-type microphone in which a capacitive vibration sensor is housed in a case.

FIG. 36 is a circuit diagram that shows an example of an output circuit of a voltage variation type.

FIG. 37 is a circuit diagram that shows an example of an output circuit of a frequency variation type.

DESCRIPTION OF REFERENCE NUMERALS 301, 304 to 307, 212, 220 Capacitive vibration sensor
32 Silicon substrate
112 Vibration electrode plate
34 Diaphragm
36, 104 Etching hole
37 Concave section
113 Opposing electrode plate
40 Acoustic hole
62 Stopper
72 Through hole

BEST MODE FOR CARRYING OUT THE INVENTION

Referring to Figures, the following description will discuss embodiments of the present invention in detail. Although the following embodiments illustrate the present invention, they are exemplary only, and the present invention is not intended to be limited thereby.

Embodiment 1

FIG. 3 is a schematic exploded perspective view that shows a capacitive vibration sensor 301 in accordance with embodiment 1 of the present invention. FIG. 4 is a plan view of the capacitive vibration sensor 301, and FIG. 5 is a cross-sectional view of the capacitive vibration sensor 301. Moreover, FIGS. 6(a), 6(b) and 6(c) are plan views that respectively show an opposing electrode plate 113, a vibration electrode plate 112 and a silicon substrate 32.

The capacitive vibration sensor 301 has a structure in which: a vibration electrode plate 112 is formed on an upper face of a silicon substrate 32, with an insulating coat film 35 interposed in between, and an electrode pad 43 used for extracting a detection signal of a sensor is provided on the upper face thereof, and an opposing electrode plate 113 is formed on the vibration electrode plate 112 located on a concave section 37 with a space interposed in between, and an electrode pad 42, used for extracting a detection signal of the sensor, is installed on the upper face thereof.

The concave section 37 having a reversed truncated pyramid shape is formed on the upper face of the silicon substrate 32, and the inner space of the concave section 37 is widened upward while it is narrowed downward, with the bottom face of the concave section 37 being sealed by the silicon substrate 32. From the viewpoint of crystal orientation, the silicon substrate 32 is constituted by a silicon substrate (silicon wafer) whose surface corresponds to the (100) plane or the (110) plane. For example, the size of the silicon substrate 32 (individually cut from a silicon wafer) is in a range of 1 to 1.5 mm in each side of square (which can be made smaller) when viewed from above, and the thickness of the silicon substrate 32 is set in a range from 400 to 500 μm, with the depth of the concave section 37 being set in a range from 200 to 300 μm.

An insulating coat film 35 made of an oxide film or the like is formed on the upper face of the silicon substrate 32, and the vibration electrode plate 112, prepared as a thin film made of polysilicon, is formed thereon. The upper face of the concave section 37 is covered with the vibration electrode plate 112 so that a portion of the vibration electrode plate 112, supported in a space above the concave section 37, is allowed to form a diaphragm (vibration area) 34. Moreover, the electrode pad 43 is formed on the vibration electrode plate 112.

A plurality of etching holes 36 are opened in the vibration electrode plate 112 within an area above the concave section 37. The diaphragm 34 is separated from the silicon substrate 32 by these etching holes 36, with holding portions 117 being left on four corners. For this reason, the diaphragm 34 is elastically supported by the holding portions 117, and an appropriate flexible property is consequently given to the diaphragm 34 having high rigidity so that by increasing the effective area of the diaphragm 34, the sensitivity of the capacitive vibration sensor 301 can be improved. Moreover, since a fluid (air) is allowed to pass through the etching holes 36, the fluid can be made well balanced on both of the surfaces of the diaphragm 34. The above-mentioned effect, obtained by separating the diaphragm 34 apart from the silicon substrate 32 except for the four corners, has been described in Japanese Patent Application Laid-Open No. 62-284233 (Patent Document 5) and Japanese Patent Application National Publication (Laid-Open) No. 9-508777 (Patent Document 6); however, the capacitive vibration sensor 301 in accordance with the present invention is characterized in that, as will be described later, the opening section, used for separating the diaphragm 34 apart therefrom, is also compatibly used as an etching hole 36 to be used for forming the diaphragm 34 from above.

In the capacitive vibration sensor 301 of embodiment 1, the etching hole 36 is formed into a virtually semi-elliptical shape. By forming the edge of the diaphragm 34 into a curved shape in this manner, it is possible to reduce the possibility of damages caused by a stress concentration upon vibration of the diaphragm 34. Here, with respect to the shape of the etching hole 36, portions of the diaphragm 34, which do not form the edges, are allowed to have a linear shape. With this arrangement, it is possible to prevent the concave section 37 from being formed wastefully at any portion other than the area of the diaphragm 34, and consequently to increase the size efficiency and the sensor strength. Moreover, since the concave section 37 to be formed through etching is always formed into a square when viewed from above due to the inherent property of silicon, it is preferable to form the etching hole 36 on a side of the square forming the concave section 37.

Here, the sensitivity of the capacitive vibration sensor 301 is varied depending on the size (or the size of the etching hole 36) of each holding portion 117 of the vibration electrode plate 112. FIG. 7 indicates frequency-sensitivity characteristics of the capacitive vibration sensor 301 in the case when the holding portion 117 is made smaller as shown by the vibration electrode plate 112 on the right side above, as well as in the case when the holding portion 117 is made larger as shown by the vibration electrode plate 112 on the right side below. When the holding portion 117 is made smaller as shown in the vibration electrode plate 112 on the right side above, the sensitivity becomes higher in a flat application band, and the low frequency response also becomes superior. However, when the holding portion 117 becomes too small, the band width in the flat application area becomes smaller. Therefore, with respect to the size of the etching hole 36, an optimal size needs to be selected through simulations or experiments, by taking into consideration the size of the holding portion 117.

The opposing electrode plate 113 has a structure in which a fixed electrode 115 made of a metal thin film is provided on the upper face of an insulating support layer 114 made of a nitride film, and a plurality of acoustic holes 40 through which vibrations of air are allowed to pass are opened in the fixed electrode 115 and the support layer 114 so as to penetrate from the upper face to the lower face. Moreover, an electrode pad 42 that is allowed to conduct to the fixed electrode 115 is provided at the end portion of the opposing electrode plate 113, and an opening 116 that exposes the electrode pad 43 of the vibration electrode plate 112 is formed thereon. The opposing electrode plate 113 having a conductive property is insulated from the vibration electrode plate 112 by the insulating coat film 35 made from an oxide film or the like in the peripheral area of the diaphragm 34, and an area thereof facing the diaphragm 34 is supported in a space with a predetermined gap being kept from the diaphragm 34.

The vibration electrode plate 112 is covered with the opposing electrode plate 113 so that an etching hole 104 is also provided in the opposing electrode plate 113 so as to etch the silicon substrate 32 from the upper face side. The etching hole 104 of the opposing electrode plate 113 is formed in to such a shape as to be included within the area of the etching hole 36 of the vibration electrode plate 112, when viewed in a direction perpendicular to the upper face of the silicon substrate 32. In the capacitive vibration sensor 301 of embodiment 1, the etching hole 104 of the opposing electrode plate 113 is formed so as to have the same shape as that of the etching hole 36 of the vibration electrode plate 112. With this arrangement, the etching holes 36 and 104 are easily formed by manufacturing processes of the capacitive vibration sensor 301, which will be described later. Moreover, the opening area of each of the etching holes 36 and 104 is made wider so that, upon etching the silicon substrate 32, an etching solution is easily directed along the outside of each of the etching holes 36 and 104, thereby making it possible to easily form a concave section 37 in the silicon substrate 32.

Since the vibration electrode plate 112 is resonated by sound vibrations to vibrate, it is formed into a thin film of, for example, 1 to 2 μm in thickness; in contrast, since the opposing electrode 113 is an electrode that is not excited to vibrate by sound vibrations, its thickness is made thicker, for example, to 10 μm.

Since a dc voltage is applied between the vibration electrode plate 112 and the opposing electrode plate 113, the respective two electrodes are respectively positively and negatively charged. For this reason, when the vibration electrode plate 112 and the opposing electrode plate 113 come too close to each other, they attract each other by mutual electrostatic attracting forces to be made tightly in contact with each other. When the vibration electrode plate 112 and the opposing electrode plate 113 have been made tightly in contact with each other, the capacitive vibration sensor 301 becomes inoperable, and a battery, which supplies a dc voltage between the vibration electrode plate 112 and the opposing electrode plate 113, also becomes running out. Moreover, the circuit connected to the capacitive vibration sensor 301 might be short-circuited to be damaged.

Therefore, the gap between the diaphragm 34 and the opposing electrode plate 113 is set to such a distance as to reduce the possibility of collision of the diaphragm 34 to the opposing electrode plate 113 when it vibrates. Moreover, one or two or more stoppers 62 (protrusions) having a protrusion length of 1 to 2 μm are allowed to protrude from the lower face of the opposing electrode 113 at positions facing the diaphragm 34. In an example shown in FIG. 5, the stoppers 62 are provided on the lower face of the opposing electrode 113; however, the stoppers 62 may be provided on the upper face of the diaphragm 34 to protrude therefrom. An insulating protective film is preferably formed on the lower face of the stopper 62. By providing the stoppers 62, the vibration electrode plate 112 and the opposing electrode plate 113 are prevented from coming closer to each other beyond a predetermined distance, thereby making it possible to solve the above-mentioned problems.

In order to reduce the stray capacitance of the capacitive vibration sensor 301, the area of the vibration electrode plate 112 is preferably made as small as possible; therefore, the area of the vibration electrode portion 112 is made greater than the concave section 37, and also made smaller than the outer shape of the silicon substrate 32. In contrast, the area of the opposing electrode plate 113 is made larger than the vibration electrode plate 112, and also made to have virtually the same size as the outer shape of the silicon substrate 32. Here, the opposing electrode plate 113 is allowed to cover the entire vibration electrode plate 112, with a space being formed between it and the vibration electrode plate 112, at least above the concave section 37.

The electrode pads 42 and 43 are formed by a metal material. The electrode pad 42 is provided on the upper face of the opposing electrode plate 113, and allowed to electrically conduct to the fixed electrode 115. The electrode pad 43, which is provided on the upper face of the vibration electrode plate 112, is insulated from the opposing electrode plate 113, and allowed to electrically conduct to the vibration electrode plate 112 (the diaphragm 34).

In this manner, in the capacitive vibration sensor 301 of embodiment 1, when vibrations of sound (compressional waves) are made incident on the upper surface, the vibrations of sound are transmitted through the acoustic holes 40 of the opposing electrode plate 113, or along the edge of the opposing electrode plate 113 to reach the diaphragm 34 to vibrate the diaphragm 34. When the diaphragm 34 starts vibrating, the distance between the diaphragm 34 and the opposing electrode plate 113 is varied to cause a change in the electrostatic capacity between the diaphragm 34 and the fixed electrode 115. Therefore, a dc voltage is preliminarily applied between the electrode pads 42 and 43, and by extracting the change in the electrostatic capacity as an electric signal, it is possible to convert sound vibrations into an electric signal, and consequently to detect the sound vibrations. Here, upon application of a dc voltage between the electrode pads 42 and 43, an electrostatic force is exerted between the vibration electrode plate 112 and the opposing electrode plate 113, and the vibration electrode plate 112 is consequently deflected toward the opposing electrode plate 113 so that the distance between the two members is shortened, thereby making it possible to improve the sensitivity.

Next, referring to cross-sectional views of FIGS. 8 to 11, the following description will discuss processes by which the capacitive vibration sensor 301 is produced by using a micromachining technique. Here, the cross-sectional views, shown in FIGS. 8 to 11, schematically express the structure for convenience of explanation, and do not express specific cross sections of the capacitive vibration sensor 301 shown in FIGS. 3 to 6.

With respect to the silicon substrate 32, a monocrystal silicon substrate whose face orientation corresponds to the (100) plane or the (110) plane is used (actually, a number of the capacitive vibration sensors 301 are manufactured on a wafer at one time) (FIG. 8(a)). An insulating coat film 35, made of a silicon oxide film, is formed on each of the upper and lower faces of the silicon substrate 32 by using a method such as a thermal oxidizing method or a CVD method (FIG. 8(b)).

Next, polysilicon (polycrystal silicon) is deposited by a CVD method on the entire surface and back surface of the insulating coat film 35 on each of the upper and lower surfaces, and a polysilicon vibration electrode plate 112 is formed on the surface side (FIG. 8(c)). Next, after a silicon oxide film 51a has been formed on each of the upper and lower surfaces (FIG. 8(d)), a resist mask 52 having a predetermined opening pattern is formed on the vibration electrode plate 112 by a photolithographic method (FIG. 9(a)), and the silicon oxide film 51a and the vibration electrode plate 112 are etched through the openings of the resist mask 52 so that the silicon oxide film 51a and the vibration electrode plate 112 are patterned into predetermined shapes, with etching holes 36 being opened therein.

After the resist mask has been removed (FIG. 9(b)), a silicon oxide film 51b serving as a sacrifice layer is deposited on the vibration electrode plate 112 by using a CVD method, a thermal oxidizing method, or the like so that the upper faces of the vibration electrode plate 112 and the silicon oxide film 51a are covered with the silicon oxide film 51b, with the silicon oxide film 51b being embedded in the etching holes 36 (FIG. 9(c)). Here, with respect to the silicon oxide film 51b serving as a sacrifice layer, PSG (SiO₂ containing phosphorous) is most preferably used. Next, a resist mask is formed so that a part of the silicon oxide film 51b serving as the sacrifice layer is etched, and the resist mask is then removed (FIG. 9(d)). In this case, on the upper surface of the diaphragm 34, openings 63 are preliminarily formed by etching at portions of the silicon oxide film 51a where the stoppers 62 are to be formed. Moreover, in other portions also, the silicon oxide film 51a and the insulating coat film 35 are removed through etching on demand.

Next, a silicon oxide film 51c serving as a sacrifice layer is laminated thereon (FIG. 10(a)). At this time, a concave section 64 having a stopper shape is formed, with a part inside an opening 63 being filled with the silicon oxide film 51c. Successively, a resist mask is again formed so that a part of the silicon oxide film 51c serving as the sacrifice layer is etched to form openings 65 (FIG. 10(b)).

Thereafter, a silicon nitride film is deposited on the silicon oxide film 51c by using a CVD method or the like so that a supporting layer 114, made of a silicon nitride film, is formed on the entire upper face of the silicon oxide film 51c (FIG. 10(c)). At this time, the inside of the concave section 64 is filled with the supporting layer 114 so that a stopper 62 is formed. Next, the supporting layer 114 on the surface, covered with a predetermined mask, is subjected to a dry etching process so that the supporting layer 114 is processed into a shape as shown in FIG. 3 so that etching holes 104 are formed with acoustic holes 40 being opened in the supporting layer 114 (FIG. 10(d)).

After the mask has been removed, the upper surface is covered with another predetermined mask, and a metal material such as chrome and copper is vapor-deposited thereon to form a fixed electrode 115 and electrode pads 42 and 43 (FIG. 11(a)). Next, a part of each of the silicon oxide films 51b and 51c inside the etching hole 36 is opened so that the silicon substrate 32 is exposed to the inside of the etching hole 36 (FIG. 11(b)). At this time, portions of the silicon oxide film 51c, which cover the side walls of the vibration electrode plate 112 are allowed to remain. Thus, the silicon oxide film 51c serving as the sacrifice layer is also allowed to function as a protective film for the vibration electrode plate 112 in an anisotropic etching process, which will be described next.

Next, by using an etchant such as an aqueous solution of TMAH (most preferable), KOH and hydrazine, the silicon substrate 32 is subjected to an anisotropic etching process through the etching holes 104 and 36. At this time, on the etching face of the silicon substrate 32, a plane having [111] orientation or an orientation equivalent to this, which is a dense plane of (100) plane silicon substrate or (110) plane silicon substrate, appears, and a concave section 37 having a truncated pyramid shape is finally generated in the silicon substrate 32 (FIG. 11(c)).

Lastly, a wet etching process using a hydrofluoric acid-based aqueous solution, or a dry etching process is carried out to remove the unnecessary silicon oxide films 51a, 51b and 51c so that the vibration electrode plate 112 and the opposing electrode plate 113 are separated from each other, thereby completing a capacitive vibration sensor 301 (FIG. 11(d)).

The following description will discuss the formation of the concave section 37 through the etching process shown in FIG. 11(c) in detail. FIGS. 12(a) and 12(a'), FIGS. 12(b) and 12(b'), FIGS. 12(c) and 12(c'), FIGS. 13(a) and 13(a'), as well as FIGS. 13(b) and 13(b') explain states in which the concave section 37, which is being etched through the respective etching holes 104, is expanding as a whole. All the FIGS. 12(a), 12(b), 12(c), 13(a) and 13(b) are plan views of the silicon substrate 32, and all the FIGS. 12(a'), 12(b'), 12(c'), 13(a') and 13(b') are cross-sectional views of the capacitive vibration sensor 301. FIGS. 12(a) and 12(a') indicate states prior to the etching process, and in FIG. 12(a), positions of the etching holes 104 are indicated by two-dot chain lines. When the etching process is started, etching proceeds from the part of each etching hole 104 so that, as shown in FIGS. 12(b) and 12(b'), a concave section 37 having a truncated pyramid shape is etched and formed in a square area that circumscribes each etching hole 104. Next, etching proceeds from each of portions at which corner sides are made in contact with each other in each concave section 37 toward the corner portion as well as toward the center so that a concave section 37 as shown in FIGS. 12(c) and 12(c') is formed, with a non-etched portion in the center being made smaller. As the etching proceeds further, as shown in FIGS. 13(a) and 13(a'), each of the peripheral portions is etched into a truncated pyramid shape, with the non-etched portion in the center being further made smaller, and finally, as shown in FIGS. 13(b) and 13(b'), the etching has proceeded up to the square area that circumscribes the entire etching hole 104 so that a target concave section 37 is formed.

As described above, the shape and the size of each etching hole 104 are determined under the condition that a circumscribing square to each etching hole 104 is made in contact with another adjacent circumscribing square; thus, a single concave section 37 can be finally formed, and consequently, it becomes possible to form a diaphragm 34 that serves as a vibration area in the vibration electrode plate 112.

Here, with respect to this manufacturing method of the capacitive vibration sensor 301, various modified examples can be proposed. For example, a commercially available SOI (silicon on insulator) wafer, as shown in FIG. 14, may be used as a starting material. This SOI wafer has a structure in which monocrystal silicon 56 (which forms a vibration electrode plate 112) is formed on a monocrystal silicon substrate 54 with a silicon oxide film 55 interposed in between; therefore, by using the SOI wafer, it becomes possible to omit the processes shown in FIGS. 8(a) to 8(c) which form insulating coat films 35 made of silicon oxide films on the upper and lower faces of the silicon substrate 32, and also form a polysilicon vibration electrode plate 112 on the insulating coat film 35 on the upper surface side.

Moreover, as shown in FIG. 15, the silicon substrate (silicon wafer) 32 may be doped with a large amount of B (boron) to form a B doped layer 57. Since the B doped layer 57 is not subjected to a wet etching process, and since this is used as an etching stop layer, it becomes possible to omit the processes of FIGS. 8(b) and 8(c), by using a wafer of this type.

In the capacitive vibration sensor 301 of embodiment 1, by etching the silicon substrate 32 from the vibration electrode plate 112 side as described above, the concave section 37 is formed in such a manner that its spatial cross-sectional area (cross-sectional area on a face in parallel with the vibration electrode plate 112) is made wider on the vibration electrode plate 112 side, and is also made narrower on the side opposing to the vibration electrode plate 112. Therefore, in the capacitive vibration sensor 301, its space inside the concave section 37 becomes narrower as it departs from the vibration electrode plate 112. In contrast, in the case of a structure of the prior art 2 shown in FIG. 2, since the silicon substrate 22 is etched from the rear face side, its spatial cross-sectional area, the through hole 27 is formed so that its spatial cross-sectional area becomes narrower on the vibration electrode plate 24 side, while it becomes wider on the side opposite to the vibration electrode plate 24; thus, the space becomes wider as it departs from the vibration electrode plate 24. As a result, in the case of the structure as shown by the prior art 2, as the silicon substrate 22 becomes thicker, the space becomes larger in comparison with the vibration electrode plate 24, with the result that the chip size of the silicon substrate 22 becomes larger due to the increased space. In contrast, in the case of embodiment 1, the space of the concave section 37 becomes smaller in comparison with the area of the diaphragm 34 so that in the case of the diaphragm 34 having the same size as the vibration electrode plate 24, the chip size can be made smaller, thereby achieving a small size of the capacitive vibration sensor 301.

Moreover, in the case when a silicon substrate having the same thickness is used, the structure as used in the prior art prolongs the etching time of the silicon substrate 22 because the through hole 27 has to be provided in the silicon substrate 22. In contrast, in the capacitive vibration sensor 301 of embodiment 1, it is only necessary to etch the concave section 37 to the middle point of the silicon substrate 32 so that the etching time of the silicon substrate 32 can be shortened, thereby making it possible to enhance the manufacturing efficiency of the capacitive vibration sensor 301.

Moreover, as shown in FIG. 11(c), the opposing electrode plate 113 is laminated on the vibration electrode plate 112 with a sacrifice layer (silicon oxide film) interposed in between, and as shown in FIG. 11(d), it is separated from the vibration electrode plate 112 by removing the sacrifice layer in the last stage of the manufacturing process; therefore, this reduces the possibility of the vibration electrode plate 112 sticking to the opposing electrode plate 113, thereby making it possible to increase the yield of the capacitive vibration sensor 301, and also to enhance the reliability thereof.

Moreover, in the structure shown in FIG. 2, since the through hole 27 is opened in the center of the silicon substrate 22 so that the silicon substrate 22 is formed into a ring shape, the rigidity of the silicon substrate 22 is lowered to make the thickness in the center (that is, the sum of the thicknesses of the vibration electrode plate 24 and the perforated member 25) thinner with respect to the entire capacitor-type microphone 21, with the result that the strength of the capacitor-type microphone 21 is lowered. In particular, since the silicon substrate 22 becomes more susceptible to twisting, the vibration electrode plate 24, which is thinner, tends to be easily damaged. In contrast, in the capacitive vibration sensor 301 of embodiment 1, since the silicon substrate 32 has a plate shape, with the concave section 37 being simply formed on the upper surface side of the silicon substrate 32, the silicon substrate 32 is allowed to have high rigidity, and the thickness of the outside appearance of the entire capacitive vibration sensor 301 is also made thicker. Therefore, the strength of the capacitive vibration sensor 301 becomes higher, and the reliability thereof is enhanced. In particular, since the rigidity of the silicon substrate 32 becomes higher, the thinner vibration electrode plate 112 held on the silicon substrate 32 becomes less susceptible to damages.

Moreover, in the capacitor-type microphone 21 shown in FIG. 2, since the vibration electrode plate 24 is exposed on the lower surface side, the vibration electrode plate 24 tends to be damaged from the back surface side and easily broken. For example, upon washing the wafer on which the capacitor-type microphone 21 has been produced, the vibration electrode plate 24 might be damaged when it receives water flows from the surface and back surface sides. In contrast, in the case of the capacitive vibration sensor 301 of embodiment 1, since the lower surface side of the vibration electrode plate 112 is covered with the silicon substrate 32, the vibration electrode plate 112 is free from damages from the back surface side so that the vibration electrode plate becomes less susceptible to breakage. For example, since, upon washing the wafer, the vibration electrode plate 112 receives water flows only from the upper surface side, it is possible to reduce the possibility of damages to the vibration electrode plate 112.

Moreover, in general, in the manufacturing processes, scratches tend to occur on the back surface side during the processing on the surface side. For this reason, in the case of a structure that requires processing on both of the two surfaces, scratches tend to occur on the surface side upon processing the back surface, resulting in defective products. In contrast, in the structure of the capacitive vibration sensor 301 in accordance with embodiment 1, since the processing is carried out only on the upper surface side, it is possible to eliminate the possibility of such damages, and consequently to increase the product yield.

In the case when the capacitive vibration sensor 301 is miniaturized, since the vibration electrode plate 112 is also made smaller, the resonance frequency of the vibration electrode plate 112 becomes excessively high, resulting in a reduction in the sensitivity to sound. However, in the capacitive vibration sensor 301 of embodiment 1, since the etching hole 36 is opened in the vibration electrode plate 112 as shown in FIG. 6(b), the rigidity of the vibration electrode plate 112 is lowered correspondingly. Moreover, the formation of the etching hole 36 in the vibration electrode plate 112 makes it possible to release an inner stress occurring in the vibration electrode plate 112, and consequently to reduce the influence from the inner stress. As a result, the vibration electrode plate 112 hardly receives influences from the inner stress so that the resonance frequency is lowered. Consequently, it becomes possible to mutually cancel the increase in the resonance frequency due to the miniaturization of the capacitive vibration sensor 301 and the reduction in the resonance frequency due to the hole opened in the vibration electrode plate 112. Moreover, since the inner stress of the vibration electrode plate 112 can be alleviated, it becomes possible to ensure the high yield and high reliability of the capacitive vibration sensor 301.

Furthermore, in the case when the concave section 37 of the silicon substrate 32 is covered with the vibration electrode plate 112, since air is enclosed in the concave section 37, the inner air serves as an air dumper, making the frequency band of the capacitive vibration sensor 301 narrower; however, by preparing the etching hole 36 (hole) in the vibration electrode plate 112, it becomes possible to externally release the air inside the concave section 37, and consequently to prevent the frequency band of the capacitive vibration sensor 301 from becoming narrower. Moreover, by opening the etching hole 36 in the vibration electrode plate 112, it is possible to restrain variations in the sensor sensitivity and the possibility of damages due to temperature changes.

Embodiment 2

FIGS. 16(a) and 16(b) are plan views that show an opposing electrode plate 113 and a vibration electrode plate 112 to be used in a capacitive vibration sensor in accordance with embodiment 2 of the present invention. In embodiment 2, with the etching hole 36 of the vibration electrode plate 112 being maintained in a semi-elliptical shape, the etching hole 104 of the opposing electrode plate 113 is formed into a slit shape having a semi-elliptical arc shape.

In the capacitive vibration sensor 301 of embodiment 1, since the etching hole 104 of the opposing electrode plate 113 has the same size as that of the etching hole 36 of the vibration electrode plate 112, the opposing electrode plate 113 might also be vibrated by a sound pressure. Moreover, since a fluid directly passes from the etching hole 104 of the opposing electrode plate 113 toward the etching hole 36 of the vibration electrode plate 112 to cause a reduction in fluid resistance within the low frequency band, the low frequency characteristic of the capacitive vibration sensor might be lowered. For this reason, in the capacitive vibration sensor in accordance with embodiment 2, the etching hole 104 of the opposing electrode plate 113 is made to have an area smaller than that of the etching hole 36 of the vibration electrode plate 112 so that, when viewed in a direction perpendicular to the upper surface of the silicon substrate 32, it is formed into a shape that is contained within the area of the etching hole 36 of the vibration electrode plate 112.

However, the area of the silicon substrate 32 to be actually etched in the silicon substrate 32 corresponds to an area in which the etching holes 104 and 36 are overlapped with each other (that is, the area of the etching hole 104); therefore, when, in order to increase the rigidity of the opposing electrode plate 113 and also to reduce the resistance of a fluid that passes through the etching hole 104, the etching hole 104 of the opposing electrode plate 113 is made smaller, concave sections that have been etched through the respective etching holes 104 are not connected to one another, with the result that there might be a failure in manufacturing a target concave section 37 in the silicon substrate 32. For this reason, in the same manner as embodiment 1, in embodiment 2 also, the shapes of the etching holes 104 are determined so that squares, each of which circumscribes each etching hole 104, are mutually overlapped with each other and so that the square that circumscribes all the etching holes 104 is allowed to have virtually the same outer shape of the opening of the concave section 37. Although detailed descriptions are omitted, a predetermined concave section 37 can be produced in the silicon substrate 32 in embodiment 2 as well, in the same manner as those shown in FIGS. 12 and 13.

Embodiment 3

FIGS. 17(a) and 17(b) are plan views that show an opposing electrode plate 113 and a vibration electrode plate 112 to be used in a capacitive vibration sensor in accordance with embodiment 3 of the present invention. In embodiment 3, with the etching hole 36 of the vibration electrode plate 112 being maintained in a semi-elliptical shape, the etching hole 104 of the opposing electrode plate 113 is allowed to have a length of ½ of that of embodiment 2.

In embodiment 3 having this structure, the etching of the concave section 37 proceeds as indicated in FIGS. 18(a) and 18(a'), FIGS. 18(b) and 18(b'), FIGS. 18(c) and 18(c'), as well as FIGS. 18(d) and 18(d'). FIG. 18(a) is a plan view that shows a capacitive vibration sensor in accordance with embodiment 3, FIGS. 18(b) to 18(d) are plan views that show the silicon substrate 32, and each of FIGS. 18(a') to 18(d') shows a cross section of the capacitive vibration sensor taken along line A-A of each of FIGS. 18(a) to 18(d). When the etching process is started from the state shown in FIGS. 18(a) and 18(a'), etching proceeds from the part of each etching hole 104 so that, as shown in FIGS. 18(b) and 18(b'), a concave section 37 having a truncated pyramid shape is etched within a square area that circumscribes the respective etching holes 104. Next, etching proceeds from each of portions at which corner sides of the respective concave sections 37 are overlapped with each other toward the corner portion as well as toward the center so that, as shown in FIGS. 18(c) and 18(c'), a concave section 37 is formed within ¼ of the area. Next, etching further proceeds from each of portions at which corner sides of the respective concave sections 37 are made in contact with each other toward a diagonal direction, and as shown in FIGS. 18(d) and 18(d'), the etching has proceeded up to the square area that circumscribes the entire etching hole 104 so that a target concave section 37 is formed.

In accordance with the capacitive vibration sensor of embodiment 3 having this structure, the rigidity of the opposing electrode plate 113 is further enhanced.

Moreover, FIGS. 19(a) and 19(b) are plan views showing an opposing electrode plate 113 and a vibration electrode plate 112 in accordance with a modified example of embodiment 3. In this modified example, the etching hole 36 of the vibration electrode plate 112 is formed into a ½ elliptical arc shape. Even when the etching hole 36 is formed into the ½ elliptical arc shape, it is allowed to exert the same effect for lowering the rigidity of the vibration electrode plate 112 as the etching hole 36 having a semi-circular shape.

Here, the shape of the concave section 37 to be formed in the silicon substrate 32 is not dependent on the shape of the etching hole 104 of its own because of inherent characteristics of the silicon substrate. FIG. 20 shows this state. FIGS. 20(a), 20(b) and 20(c) on the left side show various shapes of etching holes 104 opened in the opposing electrode plate 113, and FIGS. 20(a'), 20(b') and 20(c') on the right side respectively show the shapes of concave sections 37 formed in the silicon substrate 32 by the respective etching holes 104 of FIGS. 20(a), 20(b) and 20(c). In this manner, even when the shapes of the etching holes 104 are different, the concave section 37 having the same shape can be formed. In other words, as also disclosed in Japanese Patent Application Laid-Open No. 2001-13156 (Patent Document 7), when squares, each circumscribing each etching hole 104, are formed so that adjacent ones are mutually overlapped with each other, or made in contact with each other, a concave section 37 is formed in virtually the same area as the square that circumscribes all the etching holes 104.

The etching holes of the capacitive vibration sensor in accordance with the present invention are placed so as to allow the circumscribing squares to be made in contact with each other so as to form the above-mentioned concave section 37, and characterized in that a diaphragm is formed so as to be separated from the vibration electrode plate with holding portions on four corners being allowed to remain.

Embodiment 4

FIG. 21 is a schematic exploded perspective view that shows a capacitive vibration sensor 304 in accordance with embodiment 4 of the present invention. In embodiment 4, slit-shaped etching holes 36 and 104 are respectively opened along diagonal directions on each of corner portions of the vibration electrode plate 112 and the opposing electrode plate 113. With this arrangement, since the slit-shaped etching hole 36 is further opened in each holding portion 117 of the vibration electrode plate 112, the rigidity of the vibration electrode plate 112 is further reduced. Moreover, by forming the etching hole 104 in a diagonal direction on each corner portion of the opposing electrode plate 113, the area of each etching hole 104 having a trapezoidal shape provided on each of the four sides can be made smaller so that the rigidity of the opposing electrode plate 113 is further increased, with the flow resistance in the etching hole 104 being made higher.

FIG. 22 explains processes in which a target concave section 37 is formed by using etching holes 104 having the above-mentioned pattern. Since etching is carried out through the etching holes 104, as indicated by a one dot chain line shown in FIG. 22, concave sections 37 are formed in a square area that circumscribes the etching hole 104 in each diagonal direction, as well as in a square area that circumscribes each etching hole 104 having a trapezoidal shape. Since these concave sections 37 are made in contact with each other or overlapped with each other, etching further proceeds from each of the contact portions or the overlapped portions so that finally, a concave section 37 is formed in a square area that circumscribes all the etching holes 104, as indicated by broken lines in FIG. 33. Thus, the target concave section 37 is obtained.

FIG. 23 shows a modified example of the capacitive vibration sensor of embodiment 4. In this embodiment, the etching hole 104 that has an elongated slit shape in each diagonal direction is further shifted toward the corner side. By using this pattern, it becomes possible to obtain a target concave section 37 in the same manner as embodiment 4.

FIG. 24 shows still another modified example of embodiment 4. In this modified example, the etching hole 104 having a trapezoidal shape of embodiment 4 is changed into a half on one side to cover an area of ½ of the size thereof. In this modified example also, as indicated by one dot chain lines in FIG. 24 at first, a concave section 37 is formed in the area of the square that is circumscribed by etching hole 104 along each diagonal direction as well as in the area of the square that is circumscribed by the etching hole 104 having the trapezoidal shape. These concave sections 37 are made in contact with each other, or overlapped with each other, etching further proceeds from each of the contact portions or the overlapped portions so that finally, concave sections 37, each having an area of ¼ of the target concave section 37, are formed at two portions, as indicated by two dot chain lines in FIG. 24. Next, the target concave section 37 is formed in a square area that is circumscribed by all the etching holes 104 as indicated by broken lines in FIG. 24.

Embodiment 5

In embodiments 2 to 4, the vibration electrode plate 112 is formed on the silicon substrate 32, and the opposing electrode 113 is formed thereon; however, the order of the electrode plates may be switched so that the vibration electrode plate 112 is provided on the opposing electrode plate 113. FIG. 25 is a schematic exploded perspective view that shows a capacitive vibration sensor 305 in accordance with embodiment 5, and FIG. 26 is a cross-sectional view thereof, and in this structure, the opposing electrode plate 113 having an electrode plate 115 is formed on the silicon substrate 32 in which a concave section 37 has been formed, with vibration electrode plate 112 being formed on the opposing electrode plate 113. In this case also, when the capacitive vibration sensor 305 is viewed in a direction perpendicular to the silicon substrate 32, the etching hole 104 of the opposing electrode plate 113 is housed in an area of the vibration electrode plate 112 in which the etching hole 36 is formed, and the total area of the etching holes 104 of the opposing electrode 113 is made smaller than the total area of the etching holes 36 of the vibration electrode plate 112. Moreover, when viewed in a direction perpendicular to the silicon substrate 32, squares, each of which circumscribes the respective etching holes 104 provided in the opposing electrode plate 113, are made in contact with each other, or overlapped with each other, and a square that circumscribes all the etching holes 104 provided in the opposing electrode plate 113 is made coincident with the area of a target concave section 37. Here, in embodiment 5, an opening 116, which serves as an opening through which the electrode pad 42 of the opposing electrode plate 113 is exposed, is provided in the vibration electrode plate 112.

In embodiment 5 having this structure also, etching holes 36 are provided in the vibration electrode plate 112, with a holding portion 117 being prepared at a part, so that the rigidity of the vibration electrode plate 112 is made smaller, and by making the etching holes 104 in the opposing electrode plate 113 as small as possible, it is possible to prevent the rigidity of the opposing electrode plate 113 from becoming low to easily cause vibration and also to make the flow resistance of the etching holes 104 greater. Therefore, it becomes possible to obtain a capacitive vibration sensor 305 having a superior low frequency characteristic.

FIGS. 27(a) to 27(d), FIGS. 28(a) to 28(d), FIGS. 29(a) to 29(d) and FIGS. 30(a) and 30(b) are cross-sectional views that represent manufacturing processes of the capacitive vibration sensor 305. Referring to these Figures, the following description will discuss the manufacturing processes of the capacitive vibration sensor 305. FIG. 27(a) shows a monocrystal silicon substrate 32 (silicon wafer) whose plane orientation is (100) or equivalent to this. A $SiO_2$ coat film is formed on each of the upper and lower faces of the silicon substrate 32 by using a method, such as a thermal oxidizing method or a CVD method, so that the $SiO_2$ coat film on the upper face side is prepared as an insulating coat film 35 (FIG. 27(b)). A SiN layer is formed on the entire surface of the insulating coat film 35 on each of the upper and lower faces of the silicon substrate 32 (FIG. 27(c)) so that the SiN layer on the upper face side is prepared as a supporting layer 114, and a polysilicon layer is formed on the surface of the supporting layer 114 (FIG. 27(d)) so that the polysilicon layer on the upper face side is prepared as an electrode plate 115.

Thereafter, on the upper face side of the silicon substrate 32, the electrode plate 115 is subjected to dry etching so that the electrode plate 115 is patterned into a target shape, with acoustic holes 40 being opened in the electrode plate 115 (FIG. 28(a)). Moreover, the supporting layer 114 below the electrode plate 115 is subjected to dry etching so that an etching hole 104 and acoustic holes 40 are opened on the supporting layer 114 (FIG. 28(b)).

A sacrifice layer 132 is produced on the electrode plate 115 by depositing $SiO_2$ thereon by using a CVD method or a thermal oxidizing method (FIG. 28(c)). With respect to the sacrifice layer 132, in particular, PSG ($SiO_2$ containing phosphorous) is preferably used. Moreover, polysilicon is film-formed on the sacrifice layer 132 by the CVD method to prepare a vibration electrode plate 112 (FIG. 28(d)). Next, the vibration electrode plate 112 is subjected to dry etching so that an etching hole 36 and an opening 116 are opened therein; thus, the vibration electrode plate 112 is patterned into a target shape (FIG. 29(a)).

Next, the patterned electrode plate 112 is covered with a protective layer 133 made from $SiO_2$ (FIG. 29(b)), and the protective film 133, the sacrifice layer 132 and the insulating coat film 35 are opened within the etching hole 36 of the vibration electrode plate 112 and the etching hole 104 of the opposing electrode plate 113 to form a through hole 134 for use in etching so that the silicon substrate 32 is exposed to the bottom face of the through hole 134. Simultaneously, a window 135 used for forming an electrode pad 43 is opened in the protective film 133 so that a part of the vibration electrode plate 112 is exposed, and a window 136 used for forming an electrode pad 42 is opened in the protective film 133 and the sacrifice layer 132 at the position of the opening 116 of the vibration electrode plate 112 so that a part of the electrode plate 115 is exposed (FIG. 29(c)). Moreover, the electrode pad 43 is formed on the vibration electrode plate 112 through the window 135 by using Au, and the electrode pad 42 is formed on the electrode plate 115 through the window 136 by using Au (FIG. 29(d)).

When the silicon substrate 32 is immersed in an etching solution so as to be etched, the etching solution is allowed to pass through the through hole 134 and made in contact with the silicon 32 so that a concave section 37 is formed in the silicon substrate 32 (FIG. 30(a)). Next, when the silicon substrate 32 is immersed in an etching solution (hydrofluoric acid-based aqueous solution) used for etching $SiO_2$ of the silicon substrate 32, or subjected to dry etching, a part of each of the protective film 133, the sacrifice layer 132 and the insulating coat film 35 is etched and removed so that a space is formed between the vibration electrode plate 112 and the opposing electrode plate 113, with acoustic holes 40 being opened in the opposing electrode plate 113; thus, a capacitive vibration sensor 305 as shown in FIG. 30(b) is manufactured. In this case, the etching hole 36 of the vibration electrode plate 112 is opened in the etching hole 104 so as to be overlapped therewith; therefore, upon etching the sacrifice layer 132, the etching solution and the like are allowed to pass linearly therethrough without being held therein. Consequently, it is possible to prevent the sacrifice layer 132 from being unetched to remain between the diaphragm 34 and the opposing electrode plate 113, and consequently to prevent the diaphragm 34 and the opposing electrode plate 113 from being adhered to each other.

Embodiment 6

FIG. 31 is a cross-sectional view that shows a structure of a capacitive vibration sensor 306 in accordance with embodiment 6 of the present invention. In embodiment 6, a through hole 72 used for picking up sounds, which communicates with the bottom face of the concave section 37, is provided on the lower face of the silicon substrate 32. The through hole 72 has a truncated pyramid shape, and forms a reverse tapered shape to the concave section 37. However, the shape of the through hole 72 is not particularly limited, and the size of the opening of the through hole 72 may be made smaller on the lower face of the silicon substrate 32, and made larger on the bottom face of the concave section 37.

In embodiment 6, since the through hole 72 that communicates with the concave section 37 is provided on the bottom face of the silicon substrate 32, sound signals may be directed to the vibration electrode plate 112 also from the lower face side of the capacitive vibration sensor 6 through the through hole 72; thus, the capacitive vibration sensor 306 is allowed to receive sound vibrations from both of the surfaces, and sound collecting processes are carried out on both of the surfaces.

In order to provide the through hole 72 in the capacitive vibration sensor 306, it is only necessary to slightly modify the manufacturing processes of the capacitive vibration sensor 306 in embodiment 1. In other words, in the processes from FIG. 8(a) to FIG. 11(c), an etching window 73 may be formed in the same manner as the formation of the etching hole 36. FIG. 32 includes schematic views that show a part of the manufacturing processes of the capacitive vibration sensor 306, and FIG. 32(a) shows a process corresponding to the process of FIG. 11(b) of embodiment 1. In embodiment 1 shown in FIG. 11(b), only a part of the upper face of the silicon substrate 32 is exposed through the etching hole 36; however, in FIG. 32(a) of embodiment 6, a part of the upper face of the silicon substrate 32 is exposed through the etching hole 36, and a part of the insulating coat film 35 and the like is also etched on the lower surface of the silicon substrate 32 so that an etching window 73 is also opened.

Next, as shown in FIG. 32(b), when the silicon substrate 32 is subjected to an anisotropic etching process through the etching hole 36 and the etching window 73 by using an etchant such as an aqueous solution of TMAH (most preferable), KOH and hydrazine, as shown in FIG. 32(c), a concave section 37 having a truncated pyramid shape is formed on the upper face of the silicon substrate 32, with a through hole 72 being simultaneously opened on the lower face of the silicon substrate 32.

Lastly, a wet etching process using a hydrofluoric acid-based aqueous solution, or a dry etching process is carried out to remove the unnecessary silicon oxide film 51b and the like so that the vibration electrode plate 306 as shown in FIG. 32(d) is completed. Here, an insulating coat film 35 is allowed to remain between the silicon substrate 32 and the vibration electrode plate 112, and a silicon oxide film 51c is allowed to remain between the vibration electrode plate 112 and the opposing electrode plate 113.

In the case when the capacitive vibration sensor 306 is manufactured in this manner, since the silicon substrate 32 can be etched from both of the faces thereof to simultaneously form the concave section 37 and the through hole 72, the etching time can be shortened so that the production efficiency of the capacitive vibration sensor 306 is improved.

FIG. 33 is a cross-sectional view that shows a structure of a capacitive vibration sensor 307 in accordance with a modified example of embodiment 6. In embodiment 6, the silicon substrate 32 is etched from both of the upper face side and the lower face side to form the concave section 37 and the through hole 72; however, in the capacitive vibration sensor 307 of this modified example, by etching the silicon substrate 32 only from the upper face side, a through hole 77 having a truncated pyramid shape is formed in the silicon substrate 32.

Embodiment 7

The following description will discuss an embodiment of a capacitor-type microphone 211 in which a capacitive vibration sensor 308 of the present invention is assembled in a case. FIG. 34 shows an example in which the capacitive vibration sensor 212 of the present invention capable of receiving sound vibrations is housed in a case 213. The capacitive vibration sensor 212 and a circuit element 214 such as ICs and the like are packaged on a circuit substrate 215, and connected to circuit wiring 216 of the circuit substrate 215 through bonding wires 217. The circuit substrate 215 in which the capacitive vibration sensor 212 and the circuit element 214 have been packaged is stored on the bottom face of the case 213. The circuit wiring 216 is directed to the lower face of the case 213; thus, the capacitive microphone 211 has a structure of surface packaging type.

A vibration directing inlet 218 is opened at a position offset from the capacitive vibration sensor 212 on the upper face of the case 213, and sound vibrations directed into the case 213 from the vibration directing inlet 218 are detected by the capacitive vibration sensor 212, and the resulting signal is outputted by the circuit element 214 as a voltage change or a frequency change.

Moreover, FIG. 35 shows a capacitor-type microphone 219 in which a capacitive vibration sensor 220 in accordance with the present invention that has the through hole 72 used for collecting sound on the lower face of the silicon substrate and is capable of collecting sound vibrations from the lower face as well is housed in a case 213. This capacitor-type microphone 219 also has a structure similar to the structure of the capacitor-type microphone 211 of FIG. 34; however, in association with the sound-collecting through hole 72 provided on the lower face of the capacitive vibration sensor 220, a vibration directing inlet 221 is opened through the lower face of the case 213 and the circuit substrate 215. Here, in the embodiment of FIG. 35, a vibration directing inlet 218 may also be provided on the upper face of the case 213.

FIG. 36 is a view that shows a circuit example of the circuit element 214, and represents an output circuit of a voltage-variation type in which sound vibrations detected by the capacitive vibration sensor are converted into a change in voltage. A variable capacitor 222, shown in FIG. 36, is constituted by a vibration electrode plate and an opposing electrode plate of a capacitive vibration sensor, and the electrostatic capacity is changed by the strength of a sound (sound pressure). The variable capacitor 222 and a resistor 223 are connected in series with each other, and a fixed voltage is applied on the upper end of the resistor 223 by a dc power supply 224. When the electrostatic capacity of the variable capacitor 222 is changed due to sound vibrations, the voltage between the resistor 223 and the variable capacitor 222 is also changed; thus, the voltage at this point is used as an output, the sound vibration can be outputted as a voltage change. Here, the capacitor 225 is used for removing the dc component.

Moreover, FIG. 37 is a view that shows another circuit example of the circuit element 214, and represents an output circuit of a frequency-variation type in which sound vibrations detected by the capacitive vibration sensor are converted into a change in frequency. A variable capacitor 222, shown in FIG. 37, also represents a capacitive vibration sensor. The variable capacitor 222 and a coil 226, which serve as the capacitive vibration sensor, are connected in parallel with each other so that an LC resonant circuit is formed, and the lower end of the coil 226 is grounded so that the upper end voltage of the coil 226 is outputted through a dc cutting capacitor 225. In accordance with this circuit, when the electrostatic capacity of the variable capacitor 222 is changed due to variations in sound, the resonance frequency of the LC resonant circuit is changed so that sound vibrations can be outputted as a frequency change.

Here, the output circuit of the circuit element 214 may contain an amplifying circuit and the like.

Moreover, the vibration electrode plate can be vibrated by inputting an electric signal between the vibration electrode plate and the opposing electrode plate of the capacitive vibration sensor; therefore, to the structure of the capacitor-type microphone, by further adding an input circuit that allows the vibration electrode plate to vibrate by inputting an electric signal to the capacitive vibration sensor, the structure can also function as a speaker and an earphone in addition to the function of the microphone so that it is also used as an acoustic transducer.

Since the capacitive vibration sensor of the present invention can be used as a miniature microphone as described above, it can be applied as microphones of various apparatuses. Moreover, the capacitive vibration sensor can also be used as a sensor for detecting sounds and vibrations in devices such as a hearing aid, an artificial auris interna, an ultrasonic diagnostic apparatus, a pulse sensor, a bone density sensor and a microcapsule endoscope. Moreover, the capacitive vibration sensor can be used as FA (factory-automation) apparatuses such as a noise detector and an ultrasonic range finder, and security apparatuses such as an intrusion detecting apparatus and an indoor monitoring sensor for the aged.

Moreover, the acoustic transducer having functions as a microphone and a speaker can be used for electronic apparatuses such as a mobile telephone, a personal computer, a digital camera and an IC recorder. Furthermore, by forming the acoustic transducers into an array, an apparatus used for localizing a sound source (position estimation is carried out based upon a time difference in detection among a plurality of microphones) can be provided. When used in the water, the acoustic transducer can be applied as devices, such as a submerged microphone and a sonar.

The invention claimed is:

1. A capacitive vibration sensor comprising:
a vibration electrode plate and an opposing electrode plate that are aligned face to face with each other and placed on a surface of a semiconductor substrate so as to cover a space formed in the semiconductor substrate, wherein a plurality of etching holes are opened through the vibration electrode plate, and a part of the vibration electrode plate is separated apart from the semiconductor substrate, with a holding portion being left, by the etching holes of the vibration electrode plate, so that a diaphragm is formed; etching holes are opened on the opposing electrode plate in such a manner that each etching hole is overlapped with each of the etching holes of the vibration electrode plate, with adjacent rectangles, each circumscribing the etching hole, of the opposing electrode plate being made in contact with each other or overlapped with each other, when viewed in a direction perpendicular to the surface of the semiconductor substrate; and the space of the semiconductor substrate is formed by carrying out an etching process from the surface side of each of the two electrode plates to the opposite side of each of the two electrode plates through each of the etching holes of the opposing electrode plate and the vibration electrode plate.

2. The capacitive vibration sensor according to claim 1, wherein the etching hole of the opposing electrode plate is formed into a slit shape.

3. A microphone comprising: the capacitive vibration sensor according to claim 2, and an output circuit that converts a sound signal detected by the capacitive vibration sensor to an electric signal and outputs the resulting signal.

4. An acoustic transducer comprising: the capacitive vibration sensor according to claim 2, an output circuit that converts a sound signal detected by the capacitive vibration sensor to an electric signal and outputs the resulting signal, and an input circuit that inputs the electric signal to the capacitive vibration sensor to generate sound vibrations.

5. The capacitive vibration sensor according to claim 1, wherein the area of each etching hole on the opposing electrode plate is set to ½ of the area of each etching hole on the vibration electrode plate.

6. A microphone comprising: the capacitive vibration sensor according to claim 5, and an output circuit that converts a sound signal detected by the capacitive vibration sensor to an electric signal and outputs the resulting signal.

7. An acoustic transducer comprising: the capacitive vibration sensor according to claim 5, an output circuit that converts a sound signal detected by the capacitive vibration sensor to an electric signal and outputs the resulting signal, and an input circuit that inputs the electric signal to the capacitive vibration sensor to generate sound vibrations.

8. The capacitive vibration sensor according to claim 1, wherein the etching holes of the vibration electrode plate are formed in the center of four sides in a vibration area of the vibration electrode plate, with each of the edges being formed in an arc shape.

9. A microphone comprising: the capacitive vibration sensor according to claim 8, and an output circuit that converts a sound signal detected by the capacitive vibration sensor to an electric signal and outputs the resulting signal.

10. An acoustic transducer comprising: the capacitive vibration sensor according to claim 8, an output circuit that converts a sound signal detected by the capacitive vibration sensor to an electric signal and outputs the resulting signal, and an input circuit that inputs the electric signal to the capacitive vibration sensor to generate sound vibrations.

11. The capacitive vibration sensor according to claim 1, wherein a through hole that communicates with the space is formed in the semiconductor substrate on the side opposite to the two electrode plates.

12. A microphone comprising: the capacitive vibration sensor according to claim 11, and an output circuit that converts a sound signal detected by the capacitive vibration sensor to an electric signal and outputs the resulting signal.

13. An acoustic transducer comprising: the capacitive vibration sensor according to claim 11, an output circuit that converts a sound signal detected by the capacitive vibration sensor to an electric signal and outputs the resulting signal, and an input circuit that inputs the electric signal to the capacitive vibration sensor to generate sound vibrations.

14. A microphone comprising: the capacitive vibration sensor according to claim 1, and an output circuit that converts a sound signal detected by the capacitive vibration sensor to an electric signal and outputs the resulting signal.

15. An acoustic transducer comprising: the capacitive vibration sensor according to claim 1, an output circuit that converts a sound signal detected by the capacitive vibration sensor to an electric signal and outputs the resulting signal, and an input circuit that inputs the electric signal to the capacitive vibration sensor to generate sound vibrations.

16. A method of manufacturing a capacitive vibration sensor having a vibration electrode plate and an opposing electrode plate that are aligned face to face with each other and placed on a surface of a semiconductor substrate so as to cover a space formed in the semiconductor substrate, comprising the steps of:
forming the vibration electrode plate having etching holes above the semiconductor substrate so as to cover the surface of the semiconductor substrate;
forming the opposing electrode plate above the vibration electrode plate with a sacrifice layer interposed in between;
opening a plurality of etching holes on the opposing electrode plate in such a manner that each etching hole is overlapped with each of the etching holes of the vibration electrode plate, with adjacent rectangles, each circumscribing the etching hole, of the opposing electrode plate are made in contact with each other or overlapped with each other, when viewed in a direction perpendicular to the surface of the semiconductor substrate;
forming the space in the semiconductor substrate by wet etching or dry etching the semiconductor substrate through each of the etching holes of the opposing electrode plate and the vibration electrode plate; and
after forming the space, removing the sacrifice layer interposed between the vibration electrode film and the opposing electrode film.

* * * * *